(12) United States Patent
Mukumoto

(10) Patent No.: US 9,339,250 B2
(45) Date of Patent: May 17, 2016

(54) X-RAY CT APPARATUS

(71) Applicants: Kabushiki Kaisha Toshiba, Minato-ku (JP); Toshiba Medical Systems Corporation, Otawara-shi (JP)

(72) Inventor: Go Mukumoto, Utsunomiya (JP)

(73) Assignees: Kabushiki Kaisha Toshiba, Minato-ku (JP); Toshiba Medical Systems Corporation, Otawara-shi (JP)

(*) Notice: Subject to any disclaimer, the term of this patent is extended or adjusted under 35 U.S.C. 154(b) by 267 days.

(21) Appl. No.: 14/114,078

(22) PCT Filed: Jan. 21, 2013

(86) PCT No.: PCT/JP2013/051111
§ 371 (c)(1),
(2) Date: Oct. 25, 2013

(87) PCT Pub. No.: WO2013/114994
PCT Pub. Date: Aug. 8, 2013

(65) Prior Publication Data
US 2014/0086470 A1    Mar. 27, 2014

(30) Foreign Application Priority Data

Feb. 2, 2012    (JP) .................................. 2012-020824
Feb. 14, 2012   (JP) .................................. 2012-029341

(51) Int. Cl.
*G06K 9/00*    (2006.01)
*A61B 6/00*    (2006.01)
(Continued)

(52) U.S. Cl.
CPC .............. *A61B 6/5211* (2013.01); *A61B 6/032* (2013.01); *A61B 6/12* (2013.01); *A61B 6/466* (2013.01); *A61B 6/545* (2013.01)

(58) Field of Classification Search
None
See application file for complete search history.

(56) References Cited

U.S. PATENT DOCUMENTS 5,740,222 A    4/1998    Fujita et al.
5,748,696 A    5/1998    Fujita et al.
(Continued)

FOREIGN PATENT DOCUMENTS

CN    101150986 A    3/2008
JP    7 194616       8/1995
(Continued)

OTHER PUBLICATIONS

Combined Chinese Office Action and Search Report issued May 15, 2015 in Patent Application No. 201380002590.5 (with English translation of categories of cited documents).
(Continued)

*Primary Examiner* — Stephen R Koziol
*Assistant Examiner* — Amandeep Saini
(74) *Attorney, Agent, or Firm* — Oblon, McClelland, Maier & Neustadt, L.L.P

(57) ABSTRACT

It is to provide an X-ray CT apparatus, which can realize accuracy and efficiency in a puncturing work. An X-ray CT apparatus 1 creates volume data based on a result obtained by X-ray scanning of a subject E for medical practice with a puncture needle. The X-ray CT apparatus 1 comprises an image processor 42, and a display controller 44. The image processor 42 creates an image of the subject E obtained by scanning, which is performed in a state that the puncture needle is being inserted to the subject E, based on the volume data. The image processor 42 also creates a new planned image, based on displacement between a position of a specific region on an image based on second volume data and a position of a corresponding specific region in a first planned image, which is created based on a first volume data in advance and includes an image I of an insert passage for the puncture needle with respect to the subject E. The display controller 44 allows a display 46 to display a new planned image.

9 Claims, 34 Drawing Sheets

(51) Int. Cl.
*A61B 6/12* (2006.01)
*A61B 6/03* (2006.01)

(56) References Cited

U.S. PATENT DOCUMENTS

| | | | |
|---|---|---|---|
| 5,848,126 A | 12/1998 | Fujita et al. | |
| 6,487,431 B1 * | 11/2002 | Iwano | A61B 6/032 600/407 |
| 8,046,051 B2 | 10/2011 | Homan et al. | |
| 2002/0154801 A1 * | 10/2002 | Ohishi | G06T 3/0087 382/132 |
| 2008/0171936 A1 | 7/2008 | Homan et al. | |
| 2010/0274120 A1 * | 10/2010 | Heuscher | A61B 6/032 600/424 |

FOREIGN PATENT DOCUMENTS

| | | |
|---|---|---|
| JP | 7-194616 A | 8/1995 |
| JP | 2000 197630 | 7/2000 |
| JP | 2002 34969 | 2/2002 |
| JP | 2002 112998 | 4/2002 |
| JP | 2003 284716 | 10/2003 |
| JP | 2008 534103 | 8/2008 |
| JP | 2011 507581 | 3/2011 |

OTHER PUBLICATIONS

International Search Report Issued Feb. 12, 2013 in PCT/JP13/051111 Filed Jan. 21, 2013.

* cited by examiner

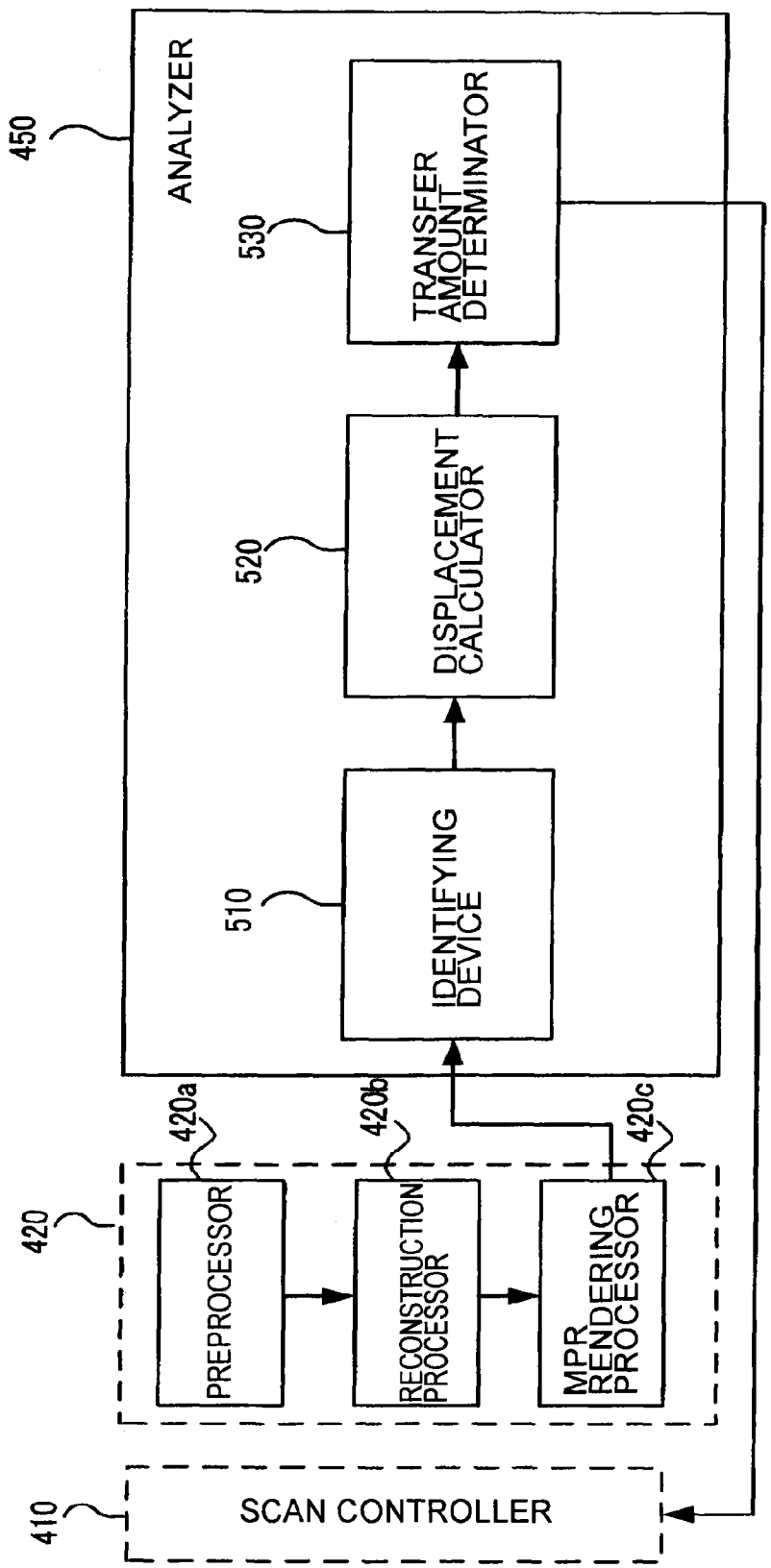

FIG. 14A
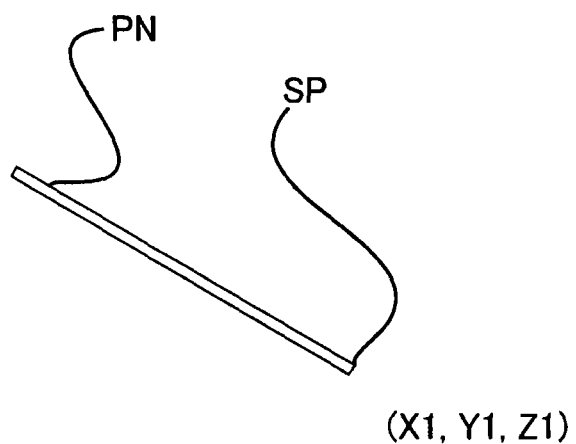
(X1, Y1, Z1)
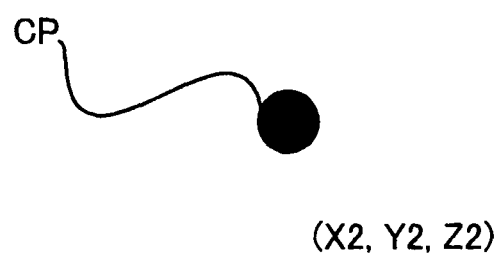
(X2, Y2, Z2)

X-RAY CT APPARATUS

TECHNICAL FIELD

The embodiments of the present invention relates to an X-ray CT apparatus.

BACKGROUND ART

An X-ray CT (Computed Tomography) apparatus is an apparatus for imaging an inside of a subject by scanning the subject using X-rays and computer processing acquired data.

Specifically, the X-ray CT apparatus exposes X-rays to a subject multiple times from different directions, detects the X-rays transmitted through the subject by an X-ray detector, and acquires a plurality of detected data. The acquired data is A/D converted by a data acquisition system, and then transmitted to a console device. The console device performs preprocessing on the detected data to create projection data. The console device then performs reconstruction processing based on the projection data, and creates tomographic image data, or volume data based on a plurality of tomographic image data. The volume data is a data set representing a three-dimensional distribution of CT values corresponding to a three-dimensional domain of the subject.

The X-ray CT apparatus is able to perform MPR (Multi Planar Reconstruction) display by rendering the volume data in an arbitrary direction. Cross section images displayed by MPR (hereinafter, refer to as "MPR images") include, for example, an axial image, a sagittal image, and a coronal image. The axial image represents a cross section orthogonal to a body axis, the sagittal image represents a cross section dividing the subject into right and left halves along the body axis, and the coronal image represents a cross section dividing the subject into ventral and dorsal halves along the body axis. An image of any arbitrary cross section (oblique image) of the volume data is also included in the MPR images.

In CT fluoroscopy (Computer Tomography Fluoroscopy) using the X-ray CT apparatus, images are created in real-time by shortening both an acquiring rate for the detected data and time required for reconstruction processing. This CT fluoroscopy is used in a case, for example, when a relationship between a puncture needle and a body site from where a specimen is collected is verified during a biopsy procedure.

When a biopsy is performed with respect to a subject while referring to MPR images, which are created based on volume data obtained by CT fluoroscopy, for example, scanning and puncturing may be performed in alternative manner. Specifically, first, MPR images of a subject are obtained by CT fluoroscopy. Doctors and the like perform puncturing while referring to the MPR images. At the time, for example, in order to verify a relationship between a puncture needlepoint and a body site from where a specimen is collected, the CT fluoroscopy is again performed when puncturing is done to some extent. The doctors and the like further proceed to the puncture as referring to MPR images obtained by the later CT fluoroscopy. The above operations are repeated until the biopsy is completed; thereby the biopsy can be performed without fail.

In addition, when a biopsy is performed by CT fluoroscopy, a puncturing plan may be made in advance. The puncturing plan is information including a preliminary set insert passage of a puncture needle with respect to a subject (hereinafter, the passage may be called "planned passage"). The puncturing plan is set, for example, by drawing a planned passage, with the help of equipment for instruction input such as a mouse, or the like, on the CT images obtained in advance before the CT fluoroscopy is performed. The doctors and the like perform puncturing with respect to the subject as referring to the CT images (planned images) indicating the planned passage and the MPR images, which are created based on volume data obtained every time X-ray scanning is performed.

PRIOR ART DOCUMENTS

Patent Documents

[Patent Document 1] Japanese Unexamined Patent Application Publication No. 2002-112998
[Patent Document 2] Japanese Unexamined Patent Application Publication No. 2002-34969

SUMMARY OF THE INVENTION

Problems to be Solved by the Invention

However, there is a case such that a posture of a subject for X-ray scanning in a puncturing plan is different from a posture of the subject for X-ray scanning in the CT fluoroscopy after the puncturing plan is made. In that case, misalignments occur between MPR images created based on volume data obtained by the X-ray scanning in the CT fluoroscopy and planned images obtained by the X-ray scanning in the puncturing plan. Therefore, it becomes difficult for operators to operate the accurate puncturing work, and efficiency of the puncturing work may fall down.

The embodiments are intended to solve the above-described problems, and the object is to provide an X-ray CT apparatus, which is able to realize accuracy and efficiency in the puncturing work.

Means of Solving the Problems

The X-ray CT apparatus of the embodiments creates volume data based on a result obtained by X-ray scanning of a subject for medical practice with a puncture needle. The X-ray CT apparatus comprises an image processor, and a display controller. The image processor creates images of the subject obtained by scanning, which is performed in a state that the puncture needle is being inserted to the subject, based on the volume data. The image processor creates a new planned image, based on displacement between a position of a specific region in an image based on a particular volume data and a corresponding position of the specific region in a planned image, which is created based on another volume data in advance and includes an image of an insert passage for the puncture needle with respect to the subject. The display controller allows a display to display the new planned image.

BRIEF DESCRIPTION OF THE DRAWINGS

FIG. 11 is a block diagram illustrating configurations of an analyzer according to the second embodiment.

FIG. 14A is a diagram for describing a difference between coordinates of a needlepoint and coordinates of a center of scanning on an MPR image.

MODES FOR CARRYING OUT THE INVENTION

First Embodiment

Refereeing to FIG. 1 to FIG. 6, an X-ray CT apparatus 1 according to a first embodiment is described. Further, since "image" and "image data" are in one-to-one correspondence, these may be classified as the same thing in the present embodiment.

<Configurations of the Apparatus>

Figure 1:
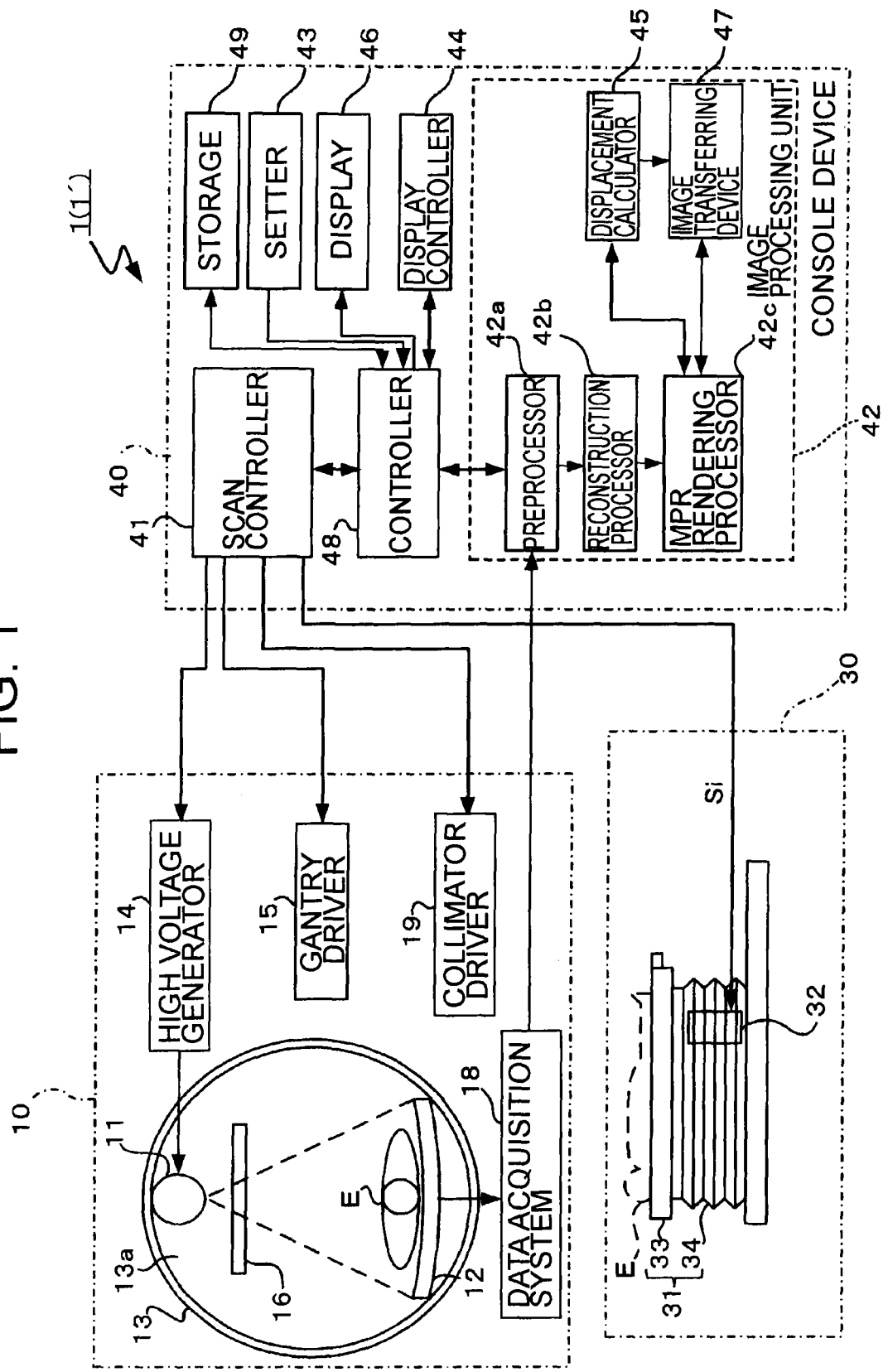
FIG. 1 is a block diagram of an X-ray CT apparatus according to a first embodiment.
Figure 2:
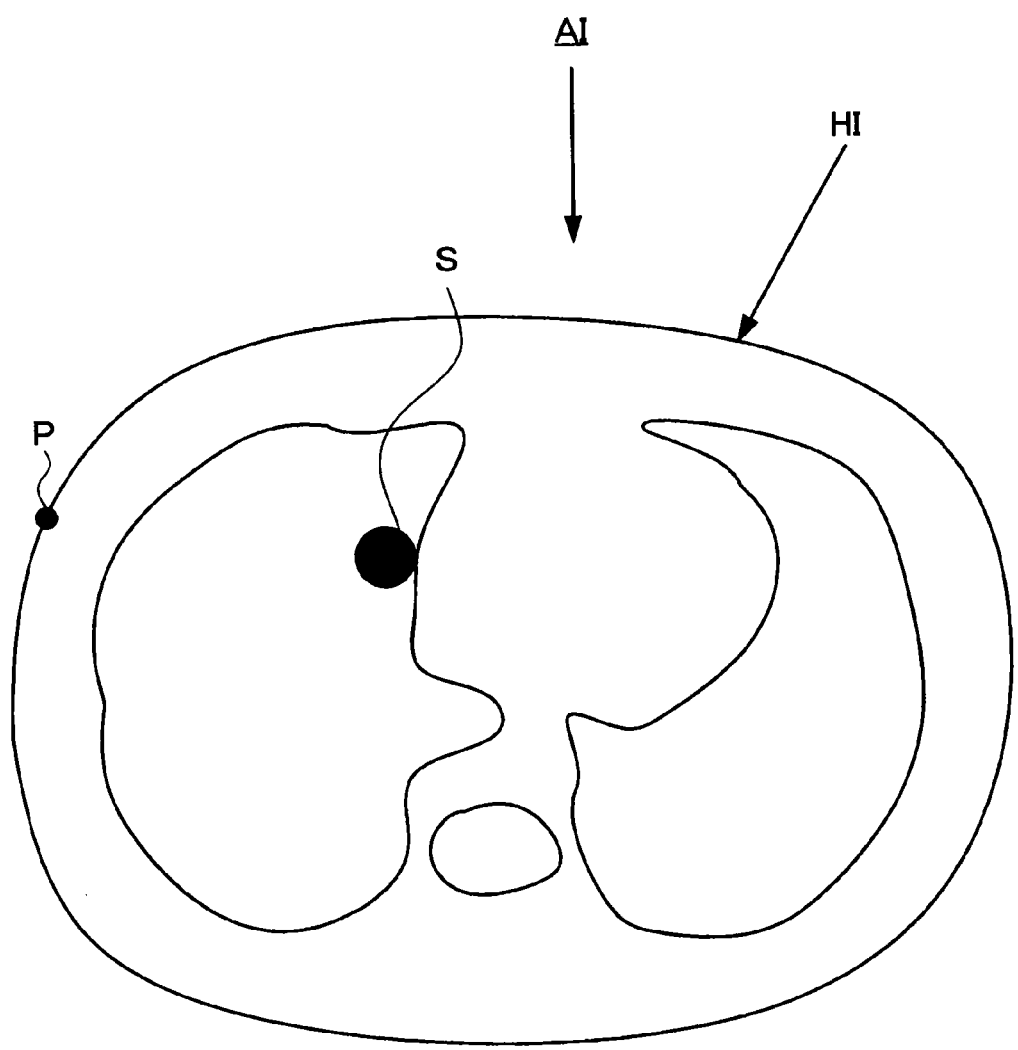
FIG. 2 is a diagram illustrating a cross-sectional image of a subject.

As shown in FIG. 1, the X-ray CT apparatus 1 is configured to include a gantry apparatus 10, a couch apparatus 30, and a console device 40.

[Gantry Apparatus]

The gantry apparatus 10 is an apparatus, which exposes X-rays to a subject E and acquires detected data of the X-rays transmitted through the subject E. The gantry apparatus 10 comprises an X-ray generator 11, an X-ray detector 12, a rotating body 13, a high voltage generator 14, a gantry driver 15, an X-ray collimator (diaphragm) device 16, a data acquisition system 18, and a collimator (diaphragm) driver 19.

The X-ray generator 11 is configured to include an X-ray vacuum tube (for example, a conical or pyramid vacuum tube to generate X-ray beams. Not shown) to generate X-rays. The X-ray generator 11 exposes the generated X-rays to the subject E.

The X-ray detector 12 is configured to include a plurality of X-ray detecting elements (not shown). The X-ray detector 12 detects the X-rays transmitted through the subject E. Specifically, the X-ray detector 12 detects X-ray intensity distribution data (hereinafter, may be called "detected data"), which indicates intensity distribution of the X-rays transmitted through the subject E, with the X-ray detecting elements, and outputs the detected data as a current signal. As the X-ray detector 12, for example, a two-dimensional X-ray detector (area detector) in which the plurality of detecting elements are arranged respectively in two directions (slice direction and channel direction) orthogonal to each other is used. The plurality of detecting elements, for example, three-hundred and twenty rows of those elements are provided along the slice direction. As descried above, by using an X-ray detector having multiple rows, a three-dimensional imaging domain having its width in the slice direction can be imaged by a single rotating scan (volume scan). Further, the slice direction corresponds to a rostrocaudal direction of the subject E, and the channel direction corresponds to a rotational direction of the X-ray generator 11.

The rotating body 13 is a member to support the X-ray generator 11 and the X-ray detector 12 facing to each other such that the subject E is sandwiched therebetween. The rotating body 13 includes an aperture 13a pierced through in the slice direction. In the gantry apparatus 10, the rotating body 13 is arranged to rotate around the subject E in a circular orbit. That is, the X-ray generator 11 and the X-ray detector 12 are arranged rotatably around the subject E along the circular orbit.

The high voltage generator 14 applies high voltage (hereinafter, "voltage" means voltage between an anode and a cathode in an X-ray vacuum tube) to the X-ray generator 11. The X-ray generator 11 generates X-rays based on the high voltage.

The gantry driver 15 allows rotationally drives the rotating body 13. The X-ray collimator device 16 includes a slit (aperture) having a predetermined width, and adjusts a fan angle of the X-rays (angular spread of the X-rays in the channel direction) and a cone angle of the X-rays (angular spread of the X-rays in the slice direction), the X-ray being exposed from generator 11. The collimator driver 19 drives the X-ray collimator device 16 so that the X-rays generated by the X-ray generator 11 to be in a predetermined form.

The data acquisition system 18 acquires the detected data from the X-ray detector 12 (each X-ray detecting element). The data acquisition system 18 also converts the acquired detected data (current signal) to a voltage signal, periodically integrates and amplifies the voltage signal, and converts the amplified voltage signal to a digital signal. The data acquisition system 18 then sends the converted detected data, which is converted to the digital signal, to the console device 40. In a case when CT fluoroscopy is performed, the data acquisition system 18 shortens the acquiring rate for the detected data.

[Couch Apparatus]

The couch apparatus 30 is an apparatus to place and transfer the subject E of an imaging target. The couch apparatus 30 comprises a couch 31, and a couch driver 32. The couch 31 comprises a couch top (plate) 33 for placing the subject E, and a base 34 for supporting the couch top 33. The couch top 33 can be moved in the rostrocaudal direction of the subject E and a direction orthogonal to the rostrocaudal direction, by the couch driver 32. That is, the couch diver 32 can inset and extract the couch top 33, on which the subject E is placed, into and from the aperture 13a of the rotating body 13. The base 34 can transfer the couch top 33 in a vertical direction (direction orthogonal to the rostrocaudal direction of the subject E) by the couch driver 32.

[Console Device]

The console device 40 is used for instruction input with respect to the X-ray CT apparatus 1. The console device 40 has functions such as reconstruction of CT image data (tomographic image data or volume data) representing internal morphology of the subject E from the detected data acquired from the gantry apparatus 10. The console device 40 is configured to include a scan controller 41, an image processor 42, a setter 43, a display controller 44, a display 46, a controller 48, and a storage 49.

The scan controller 41, the image processor 42, the display controller 44, and the controller 48 are configured from, for example, not shown processors such as CPU (Central Processing Unit), GPU (Graphic Processing Unit), and ASIC (Application Specific Integrated Circuit), and not shown storages such as ROM (Read Only Memory), RAM (Random Access Memory), and HDD (Hard Disc Drive). In the storage, control programs for executing functions of each device are stored. The processors such as CPU execute the functions of each device by executing each program stored in the storage.

The scan controller 41 controls a variety of operations related to X-ray scanning. For example, the scan controller 41 controls the high voltage generator 14 to apply high voltage to the X-ray generator 11. The scan controller 41 controls the gantry driver 15 to rotational drive the rotating body 13. The scan controller 41 controls the collimator driver 19 to operate the X-ray collimator device 16. The scan controller 41 also controls the couch driver 32 to transfer the couch top 33.

The image processor 42 executes a variety of processes on the detected data sent from the gantry apparatus 10 (data acquisition system 18). The image processor 42 is configured to include a preprocessor 42a, a reconstruction processor 42b, a MPR rendering processor 42c, a displacement calculator 45, and an image transferring device 47.

The preprocessor 42a performs preprocessing such as a logarithmic conversion process, offset correction, sensitivity correction, and beam hardening correction, with respect to the detected data detected by the gantry apparatus 10 (X-ray detector 12), and creates projection data.

The reconstruction processor 42b creates CT image data (tomographic image data or volume data) based on the projection data created by the preprocessor 42a. For reconstructing of the tomographic image data, for example, an arbitrary method may be used, the method including the two dimensional Fourier transform method, the Convolution-Back-projection method, and the like. The volume data is created by performing an interpolate process on the plurality of reconstructed tomographic image data. For reconstructing of the volume data, for example, an arbitrary method may be used, the method including a cone-beam reconstruction method, a multi-slice reconstruction method, an enlarge reconstruction method, and the like. Reconstruction of extensive volume data can be achieved by volume scanning using the X-ray detector having multiple rows as described above. In addition, when CT fluoroscopy is performed, since the acquiring rate for the detected data is set short, reconstruction time required for the reconstruction processor 42b is shortened. Accordingly, the CT image data can be created in real-time corresponding to scanning.

The MPR rendering processor 42c creates a plurality of MPR images (axial image, sagittal image, and coronal image of three orthogonal cross sections) by rendering the volume data, which is created (reconstructed) by the reconstruction processor 42b, in an arbitrary direction.

Further, the MPR rendering processor 42c can create an oblique image, which is an image of any arbitrary cross section of the volume data, as a MPR image. For example, draw a line segment where a cross section is desired on a MPR image displayed on the display 46. The MPR rendering processor 42c creates an oblique image by rendering the volume data in a predetermined direction according to the line segment as a standard.

The setter 43 sets a predetermined set image with respect to an image based on a first volume data. The "set image" is a desired image drawn on the image based on the first volume data. Foe example, when a biopsy is performed on the subject E, there is a case such that an insert passage plan for a puncture needle (in which route the puncture needle should be inserted. That is a planned passage) is drawn on an image in advance. The drawn image (image of the planned passage) is an example of the set image. The set image may alternatively be an image marked a target site (lesion site or the like) with a circle or ellipse on the image. Hereinafter, the processes of the setter 43 and the display controller 44, from setting of a set image until displaying a planed image on which the set image is drawn on the display 46, are described with reference to FIG. 2, FIG. 3, and FIGS. 4A to 4C.

A plurality of axial images is created based on the first volume data obtained by a first scanning at particular timing, and an axial image (first subject image HI), on which a target site S is drawn, is chosen from the above images. The first subject image HI is displayed on the display 46 by the display controller 44 (see FIG. 2). Since any puncture needle is inserted at this stage, no puncture needle is drawn on the first subject image HI yet in FIG. 2. Next, the setter 43 sets a set image I for allowing drawing to be performed on the first subject image HI.

Figure 3:
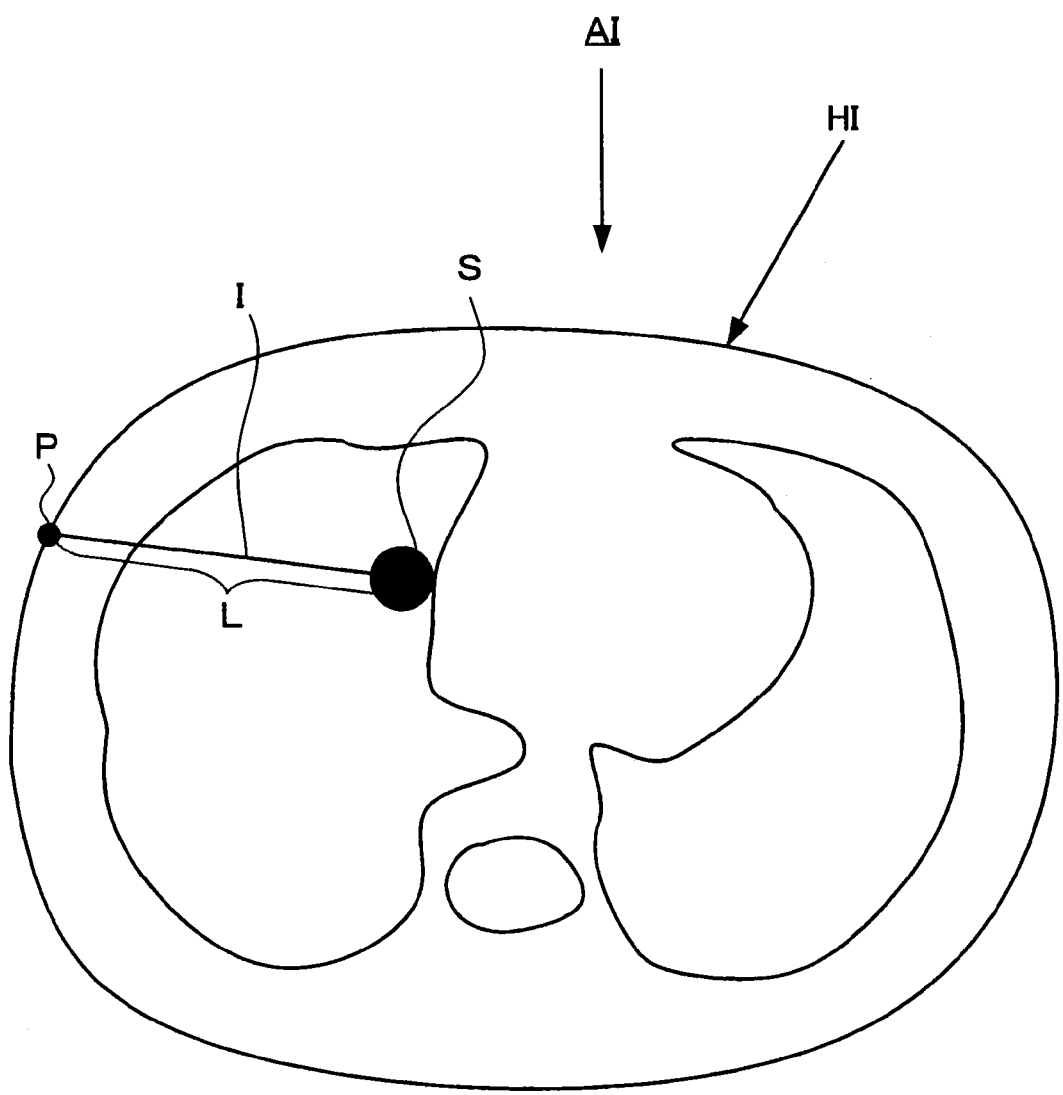
FIG. 3 is a diagram illustrating a planned image, which is the cross-sectional image of the subject on which a planned passage is drawn.

Here, a specific setting method for the set image is described with reference to FIG. 3. An operator designates, with respect to the first subject set image HI displayed on the display 46, two points that is a position of the target site S (lesion site or the like), where a biopsy is performed using a not-shown input device, and the like provided on the X-ray CT apparatus or the like, and an insert position P of the puncture needle on the surface of the subject. The setter 43 calculates a shortest distance L connecting these two points, and sets the line segment representing the shortest distance L as the set image I. The set image I set earlier is drawn on the first subject image HI by the display controller 44.

The operator may directly draw a line segment, and the like representing a planned passage on the first subject image HI using the input device and the like. In that case, the setter 43 sets the line segment drawn as above as the set image I. Alternatively, by performing an image analysis process such as a region growing method, and the like with respect to the first volume data, the setter 43 may calculate a position of the target site (lesion site) and a position closest from the target site on the subject surface. In addition, the setter 43 may then calculate the line segment connecting these two positions, and set the line segment as the set image I.

Figure 4A:
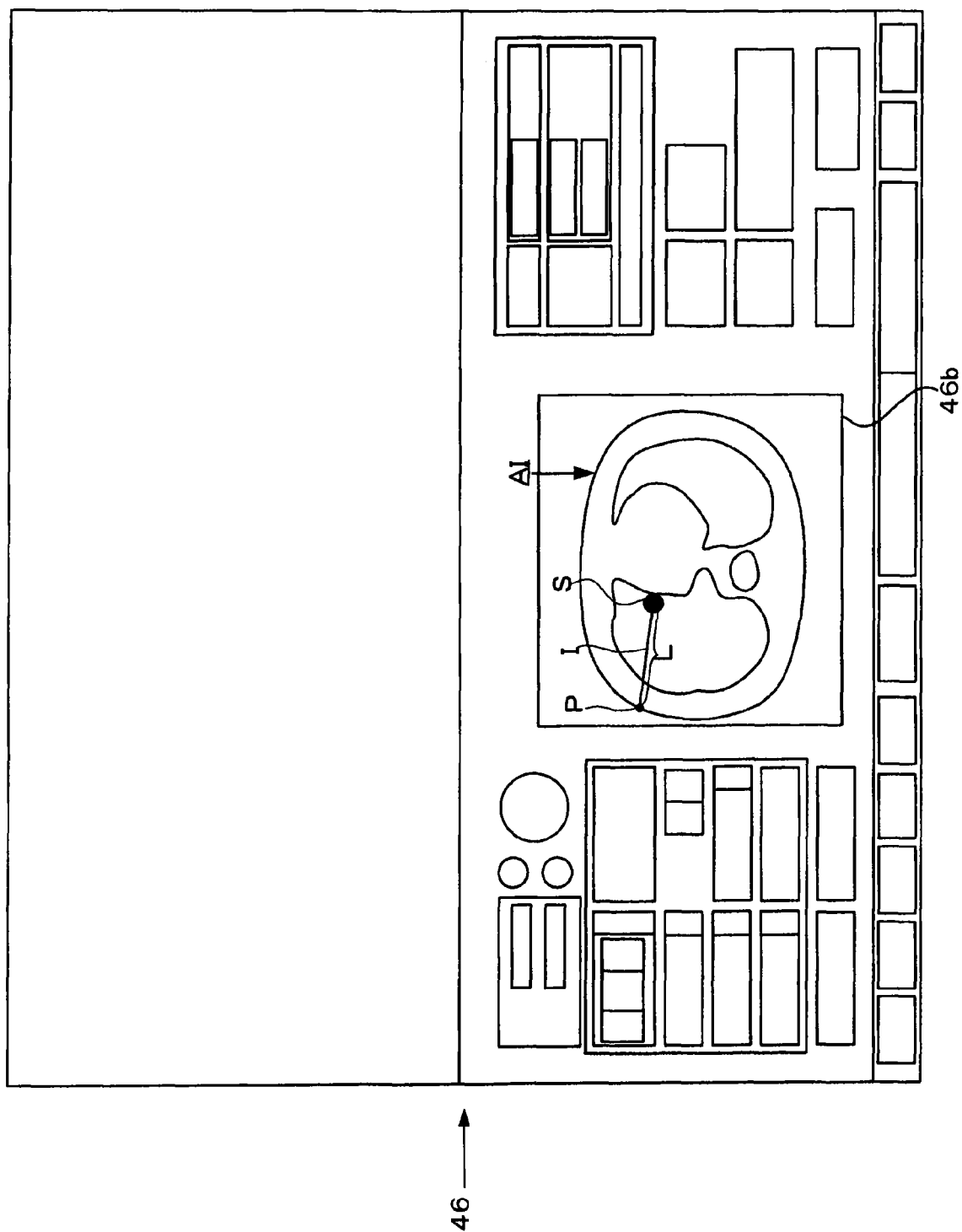
FIG. 4A is a diagram illustrating a screen of a display displaying the planned image.

A first axial image AI, that is the first subject image HI on which the set image I is drawn (hereinafter, refers to as a "first planned image") is displayed on a display screen 46b of the display 46 by the display controller 44 (see FIG. 4A). The first planned image AI can be used as a reference image in a case when puncturing and the like is performed with respect to the subject E. At the time the first planned image AI is displayed, as shown FIG. 4A, a MPR image based on a later-described second volume data is not yet displayed on the display 46.

The setter 43 also determines a position of the set image I (coordinate values. Hereinafter, it may refer to as a "set position") on the first subject image HI. The set image I and the set position are stored in the storage 49, which will be described later.

The storage 49 is configured from semiconductor memory devices such as RAM, ROM, and the like. The storage 49 stores set images, set positions thereof, as well as detected data, projection data, and CT image data after reconstruction processing. The storage 49 also stores a transferred (coordinate-converted) MPR image based on displacement calculated by the displacement calculator 45, which will be described later. The MPR image after transferring may be stored temporarily in a not-shown storage (for example, a cache memory) in the controller 48. That is, when the image is displayed live, the cache memory is used to display.

The controller 48 performs a total control of the X-ray CT apparatus 1 by controlling the operations of the gantry apparatus 10, the couch apparatus 30, and the console device 40. For example, the controller 48 controls the scan controller 41 to allow execution of preliminarily scanning and main scanning with respect to the gantry apparatus 10 and acquisition of the detected data. The controller 48 also controls the image processor 42 to allow execution of various processes (preliminarily process, reconstruction process, and the like) with respect to the detected data. Alternatively, the controller 48 controls the display controller 44 to allow the display 46 to display images based on the CT image data, and the like, stored in the storage 49.

The display controller 44 performs various controls over image display. For example, the display controller 44 controls the first planned image AI to be displayed on the display screen 46b of the display 46, the MPR image (axial image, sagittal image, coronal image, or oblique image. Axial image in the present embodiment) created by the MPR rendering processor 42c and the like to be displayed on the display 46.

After the first planned image AI is displayed on the display screen 46b of the display 46 (see FIG. 4A) by the display controller 46, the operator proceeds with a punctuating work using a puncture needle PN. When the punctuating work is done to a certain degree, a second scanning is started with respect to the subject E. The second scanning is performed different timing from the first scanning. The display controller 44 displays, as shown FIG. 4B, an axial image (hereinafter, refers to as a "second axial image") AI' based on second volume data obtained by the second scanning on a display screen 46a of the display 46 (see FIG. 4B). In addition, the timing in performing the second scanning is synchronized with respiration.

Further, in the present embodiment, it is assumed that the numbers of tomographic image data and the numbers of pixels of the first volume data and the second volume data are set to be equal, the tomographic image data being the basis of those volume data. It is also assumed that the imaging conditions (capturing position, rotation speed of the rotating body 13, and the like) for the first scanning and the second scanning are set to be equal. That is, it is assumed that the first volume data and the second volume data are in the same coordinate system.

Figure 4B:
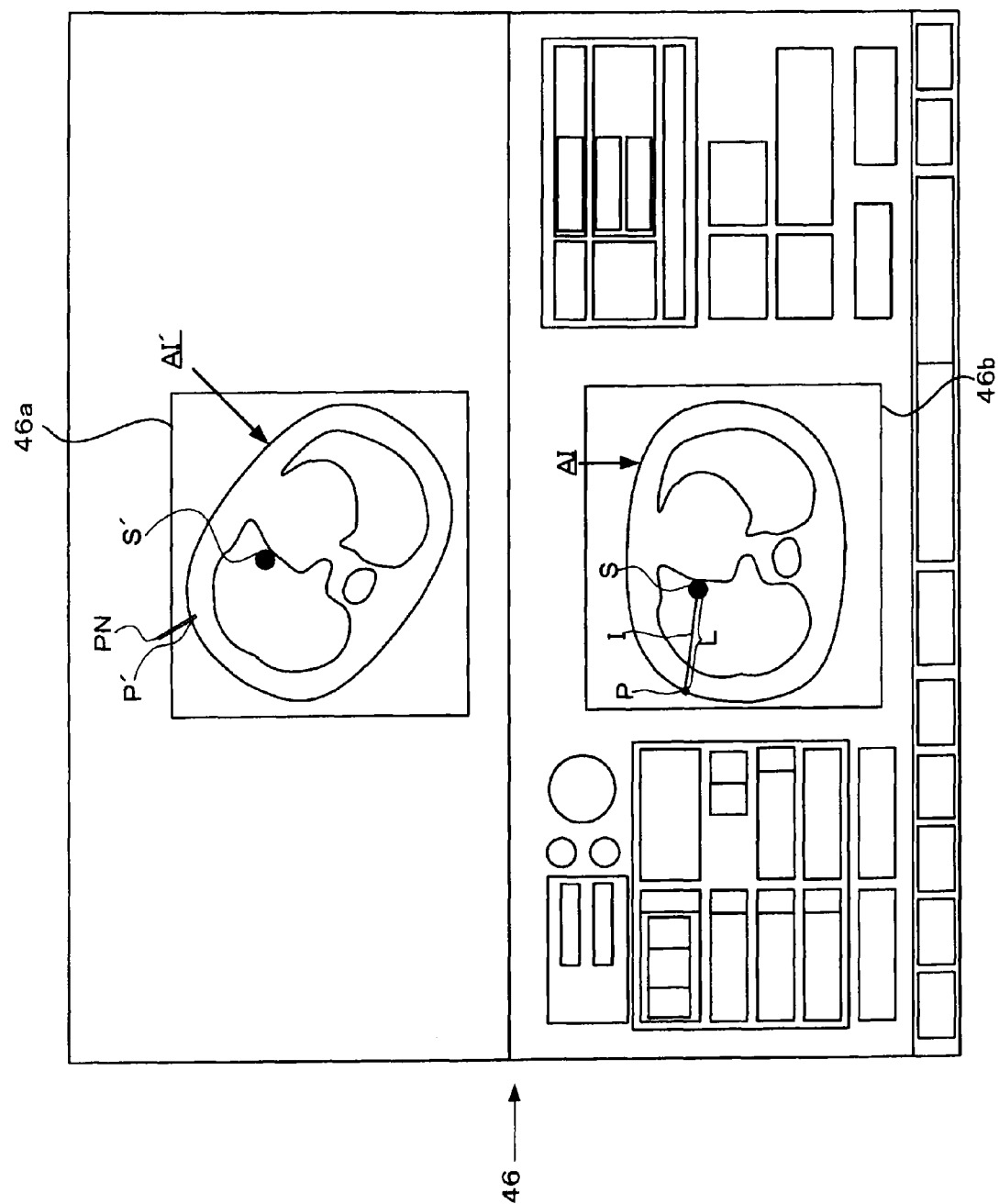
FIG. 4B is a diagram illustrating a screen of the display according to the first embodiment.

There is a case that the placed position of the subject E is changed, because of the body move of the subject E, before the second scanning is started. When the scanning is performed in that state, the second axial image AI' looks different form the first planned image AI, as shown in FIG. 4B. For example, in the example in FIG. 4B, when focusing on the rotational angle, the second axial image AI' is the image, which is the first planned image AI rotated by a predetermined angle in a clockwise direction. In this case, since the first planned image AI and the second axial image AI' are seen differently, it is difficult for the operator to perform a punctuation work efficiently.

Therefore, in the present embodiment, the displacement calculator 45 of the image processor 42 calculates displacement (transfer distance and rotational angel) between a position of a specific region in the second axial image AI' (for example, a target site position S' and an insert position P' of the puncture needle) and a position of a specific region in the first planned image AI (for example, a target site position S and an insert position P of the puncture needle).

Figure 5A:
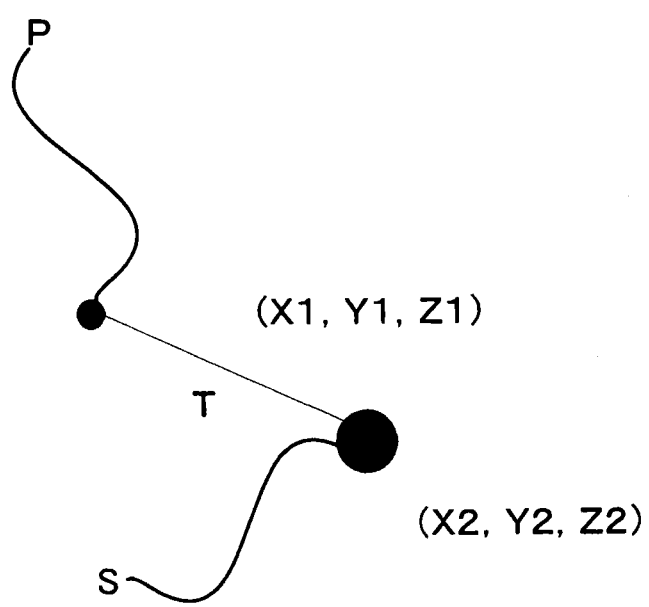
FIG. 5A is a diagram complementing a description of image transfer according to the first embodiment.
Figure 5B:
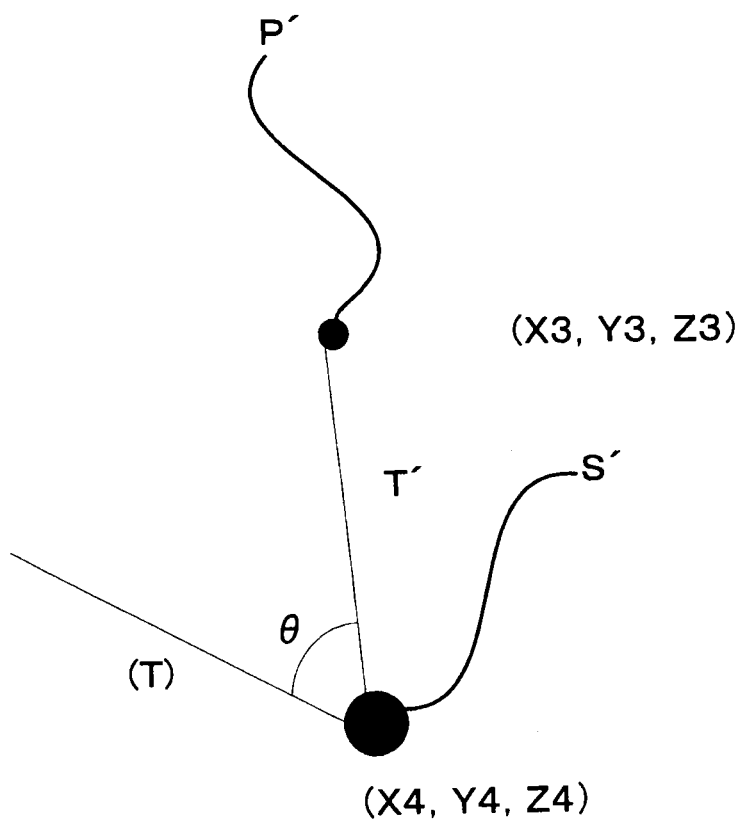
FIG. 5B is a diagram complementing the description of image transfer according to the first embodiment.

Next, an example of calculation by the displacement calculator 45 is described with reference to FIG. 5A and FIG. 5B. Specifically, the displacement calculator 45 calculates the transfer distance, as shown in FIG. 5A and FIG. 5B, by taking a difference (X4−X2, Y4−Y2, Z4−Z2) between coordinate values (X4, Y4, Z4) of the target site S' in the second axial image AI' and coordinate values (X2, Y2, Z2) of the target site S in the first planned image AI, and a difference (X3−X1, Y3−Y1, Z3−Z1) between coordinate values (X3, Y3, Z3) of the insert position P' in the second axial image AI' and coordinate values (X1, Y1, Z1) of the insert position P in the first planned image. For a rotational angle θ, the displacement calculator 45 determines skew in the transfer direction with respect to the reference direction (a rotational angle θ), based on a direction of a line segment T connecting the target site S and the insert position P (a reference direction) and a direction of a line segment T' connecting the target site S' and the insert position P' (a transfer direction). In the example in FIG. 5A and FIG. 5B, the displacement between the images is determined by the coordinates of the two points and the directions (angles); however, the displacement may be calculated based on the displacement of the coordinate values of the puncture needle PN.

The image transferring device 47 transfers (parallel transfers and rotational transfers) only the set image I in the first planned image AI, based on the calculated displacement. As a transferring method, other than the method by parallel transferring and rotational transferring as stated above, coordinate transformation by a publicly know affine transformations may be performed.

A set image I' after transferring is stored in the storage 49. The image processor 42 reads the set image I' after transferring out from the storage 49, and creates a second planned image AI' by drawing the set image I' after transferring, which is read out earlier, on a second subject image (image which is the second axial image A' without the puncture needle PN) (see FIG. 4C). The display controller 44 allows the display 46 to display the second planned image AI", in place of the first planned image AI, as a new planned image. In addition, the positions (coordinate values) of the target site S' and a target site S" are the same, and the positions (coordinate values) of the insert position P' and an insert position P" are also the same.

The display 46 is configured with an arbitrary display device such as LCD (Liquid Crystal Display), a CRT (Cathode Ray Tube) display, or the like. For example, an MPR image obtained by performing a rendering process on volume data is displayed on a display 46a of the display 46. In the present embodiment, as shown in FIG. 4B, the example displaying the axial image is shown; however, a sagittal image, a coronal image, or an oblique image may be displayed.

<Operations>

Figure 6:
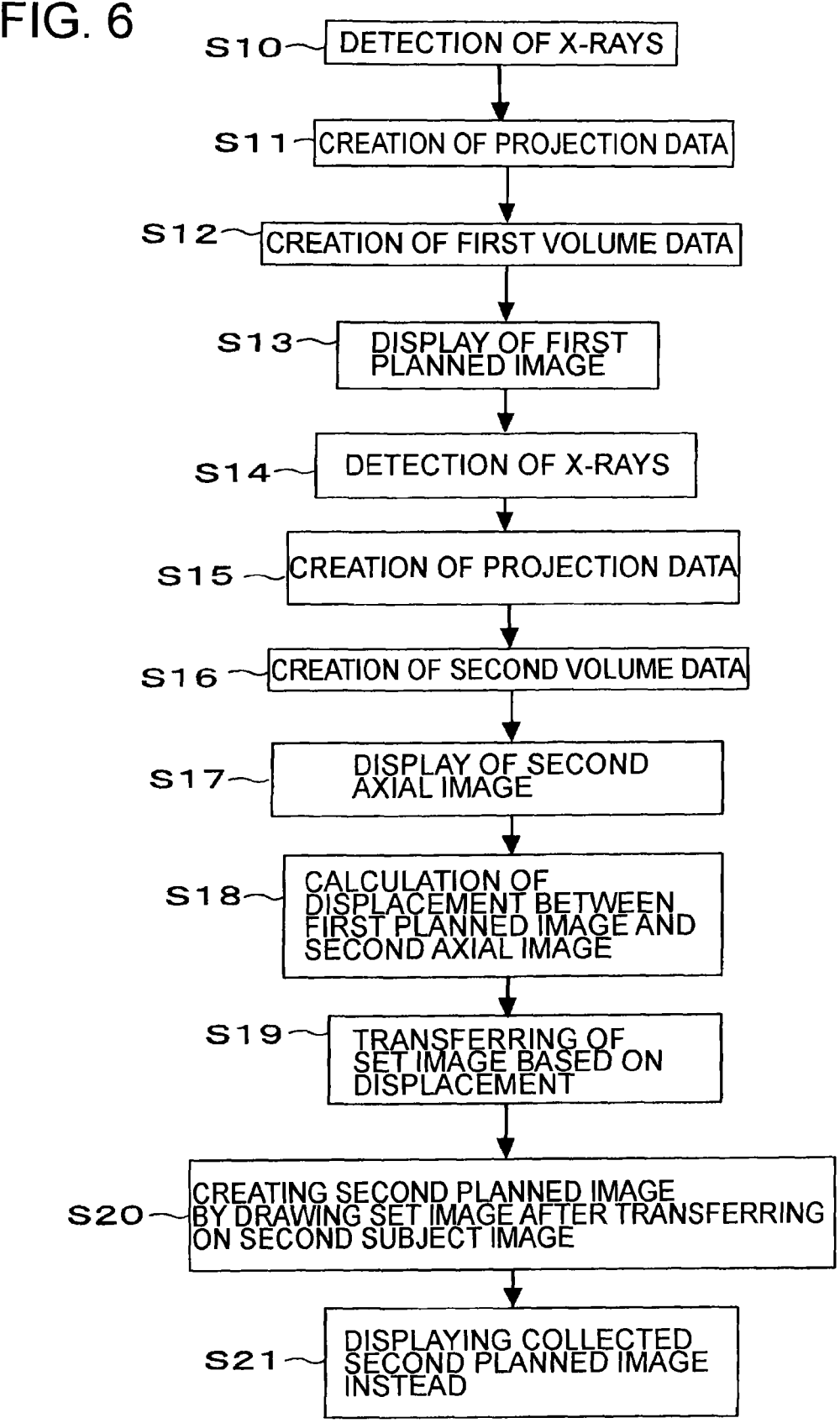
FIG. 6 is a flowchart illustrating an operation outline of the X-ray CT apparatus according to the first embodiment.

Next, operations of the X-ray CT apparatus 1 according to the present embodiment is described with reference to FIG. 6. Here, operations in a case such that a biopsy is performed with CT fluoroscopy after a planned passage for a puncture needle is created are described. FIG. 6 is a flowchart illustrating a flow of the operations in such the case.

Before performing a biopsy, the X-ray CT apparatus 1 firstly performs X-ray scanning (first scanning) with respect to a subject E, and then creates first volume data.

(S10: Detection of the X-Rays)

Specifically, the X-ray generator 11 exposes X-rays to the subject E. The X-ray detector 12 detects the X-rays transmitting through the subject E, and obtains detected data. The detected data detected by the X-ray detector 12 is acquired by the data acquisition system 18, and sent to the image processor 42 (preprocessor 42a).

(S11: Creation of Projection Data)

The preprocessor 42a performs preprocessing such as a logarithmic conversion process, offset correction, sensitivity correction, and beam hardening correction, with respect to the obtained detected data, and creates projection data. The created projection data is sent to the reconstruction processor 42b based on the control of the controller 48.

(S12: Creation of First Volume Data)

The reconstruction processor 42b creates a plurality of tomographic image data based on the projection data created in S11. The reconstruction processor 42b also creates first volume data by performing an interpolate process on the plurality of tomographic image data.

(S13: Display of First Planned Image)

The MPR rendering processor 42c creates a plurality of MPR images (axial images in the present embodiment) by performing a MPR rendering process on the first volume data created in S12. An axial image (first subject image HI), on which the subject site S is drawn, is selected from the plurality of axial images. The selection may be done by automatic selection or manual selection of any publicly known methods. In the selected first subject image HI, a line segment L connecting the position of the subject site S and an insert position P of a puncture needle PN is set as a set image I by the setter 43. The image processor 42 creates the first planned image AI by drawing the set image I, which is set earlier, on the first subject image. The display controller 44 then allows the first planned image to be displayed on the display screen 46b of the display 46. Further, the setter 43 sends the set image and the coordinate values thereof to the storage 49. The storage 49 stores the set image, and the coordinate values thereof.

Subsequently, the operator starts performing a biopsy with respect to the subject E while referring to the first planned image AI. After the biopsy is done to some extent (after the puncture needle is inserted with respect to the subject E), the X-ray CT apparatus 1 again performs X-ray scanning (second scanning) with respect to the subject E, in order to verify a puncture state (whether the puncture needle is traveled along the planned passage, and the like). The X-ray CT apparatus 1 then creates volume data (second volume data) based on the projection data (S14 to S16).

(S14: Detection of X-Rays)

First, in a similar manner as in the first scanning, the X-ray generator 11 exposes X-rays with respect to the subject E. The X-ray detector 12 detects the X-ray transmitted through the subject E, and acquired the detected data.

(S15: Creation of Projection Data)

The reconstruction processor 42b performs preprocessing such as a logarithmic conversion process, offset correction, sensitivity correction, beam-hardening correction, and the like, with respect to the obtained detected data, and creates projection data.

(S16: Creation of Second Volume Data)

The reconstruction processor 42b creates second volume data by performing an interpolate process on a plurality of tomographic image data created based on the projection data created in S15.

(S17: Display of Second Planned Image)

The MPR rendering processor 42c creates a plurality of MPR images by performing the rendering process on the second volume data created in S16. The display controller 44 displays an image of the cross section (second axial image AI'), which is the same as the one of the first planned image AI, on the display screen 46a of the display 46.

(S18: Calculation of Displacement Between First Planned Image and Second Axial Image)

Next, the displacement calculator 45 calculates displacement (transfer distance and rotational angel) between the position of a specific region in the second axial image AI' (the position of the target site S' and the insert position P' of the puncture needle PN) and the position of a specific region in the first planned image AI (the position of the target site S and the insert position P of the puncture needle PN).

(S19: Transferring of Set Image Based on Displacement)

Specifically, as shown in FIG. 6, the displacement calculator 45 calculates the transfer distance by taking a difference (X4−X2, Y4−Y2, Z4−Z2) between coordinate values (X4, Y4, Z4) of the target site S' in the second axial image AI' and coordinate values (X2, Y2, Z2) of the target site S in the first planned image AI, and a difference (X3−X1, Y3−Y1, Z3−Z1) between coordinate values (X3, Y3, Z3) of the insert position P' in the second axial image AI' and coordinate values (X1, Y1, Z1) of the insert position P in the first planned image AI. For the rotational angle, the displacement calculator 45 determines inclination of the transfer direction with respect to the reference direction (a rotational angle θ), based on the direction of the line segment T connecting the target site S and the insert position P (a reference direction) and the direction of the line segment T' connecting the target site S' and the insert position P' (a transfer direction). Next, the image transferring device 47 transfers (parallel transfers and rotational transfers) only the set image I in the first planned image AI, based on the calculated displacement. The set image I' after transferring is stored in the storage 49.

(S20: Creating Second Planned Image by Drawing Set Image after Transferring on Second Subject Image)

Figure 4C:
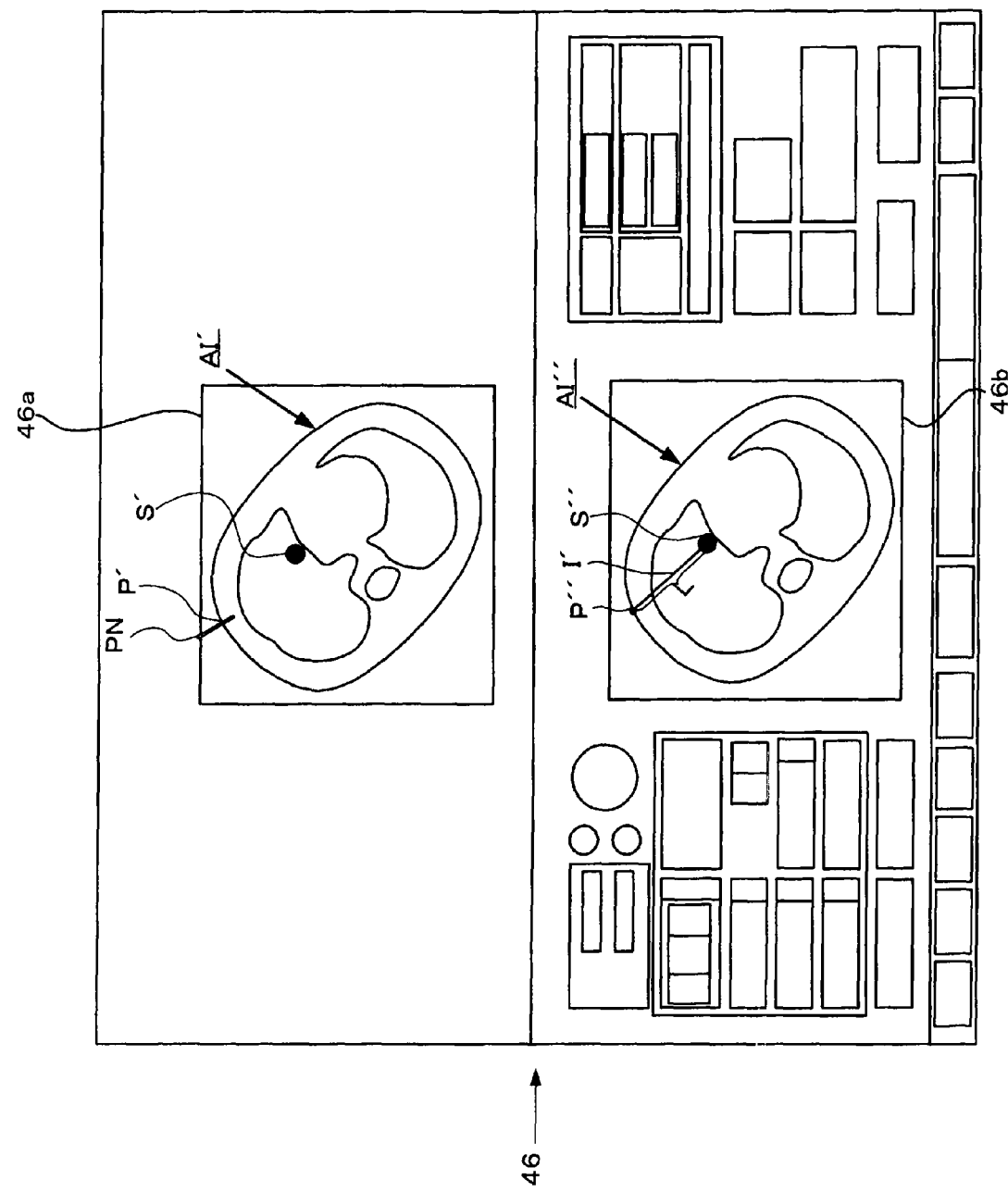
FIG. 4C is a diagram illustrating a screen of the display according to the first embodiment.

The image processor 42 reads the set image I' after transferring from the storage 49, and creates a second planned image AI" by drawing the set image I' after transferring, which is read out earlier, on a second subject image (image which is the second axial image A' without the puncture needle PN) (see FIG. 4C).

(S21: Displaying Collected Second Planned Image Instead)

The display controller 44 displays the second planned image AI", in place of the first planned image AI, as a new planned image on the display screen 46b of the display 46.

The operator proceeds with the next puncturing work while referring to the new planned image. The new planned image has a function to call attention to a case such that the insertion angel and the insertion distance of the puncture needle are changed.

<Effect>

The X-ray CT apparatus 1 of the present embodiment creates volume data based on a result obtained by X-ray scanning of the subject E for medical practice with the puncture needle PN. The X-ray CT apparatus 1 comprises the image processor 42, and the display controller 44. The image processor 42 creates an image of the subject E obtained by scanning, which is performed in a state that the puncture needle PN is being inserted to the subject E, based on the volume data. The image processor 42 also creates a new planned image (second planned image) AI", based on displacement between a position of a specific region in an image based on the second volume data and a position of a corresponding specific region in the first planned image AI, which is created based on the first volume data in advance and includes the image I of an insert passage for the puncture needle with respect to the subject E. The display controller 44 allows the display 46 to display the new planned image AI".

Specifically, the display controller 44 allows the display 46 to display a new planned image AI" in place of the first planned image AI so as to cancel the displacement.

In this way, when the position of the subject E is displaced, the display controller 44 can transfer the image (set image) of the insert passage of the puncture needle based on the displacement, and allow the display to display the image, which is the second subject image on which the set image after transferring is drawn, as the new planned image (second planned image). Thus, since there is no misalignment occurs between the image based on the second volume data (second axial image), and the new planned image after replacement, there is no chance for both images to be looked different.

Therefore, by referring to the replaced new planned image, image analysis based on the second volume data becomes easier. That is, it is possible to realize accuracy and efficiency in the puncturing work.

Modified Example 1

In the above present embodiment, is was described that the set image I' is created based on the displacement due to the body move of the subject E, the set image I' being an image created by transferring the set image I representing the insert passage of the puncture needle PN, and the image (second planned image AI" in FIG. 4B) drawing the set image I' on the second subject image (tomographic image of the subject E on the second axial image) is displayed on the display 46 as a new planned image. In contrast, an X-ray CT apparatus 1' according to a present modified example (see FIG. 1) transfers a second subject image configuring a second axial image based on second volume data so as to cancel the displacement due to the body move of the subject E, and allows the display 46 to display an image (second planned image AI'" in FIG. 7) in place of the first planned image AI, the image (second planned image AI'") superimposing and displaying the set image I on the transferred second subject image.

Figure 7A:
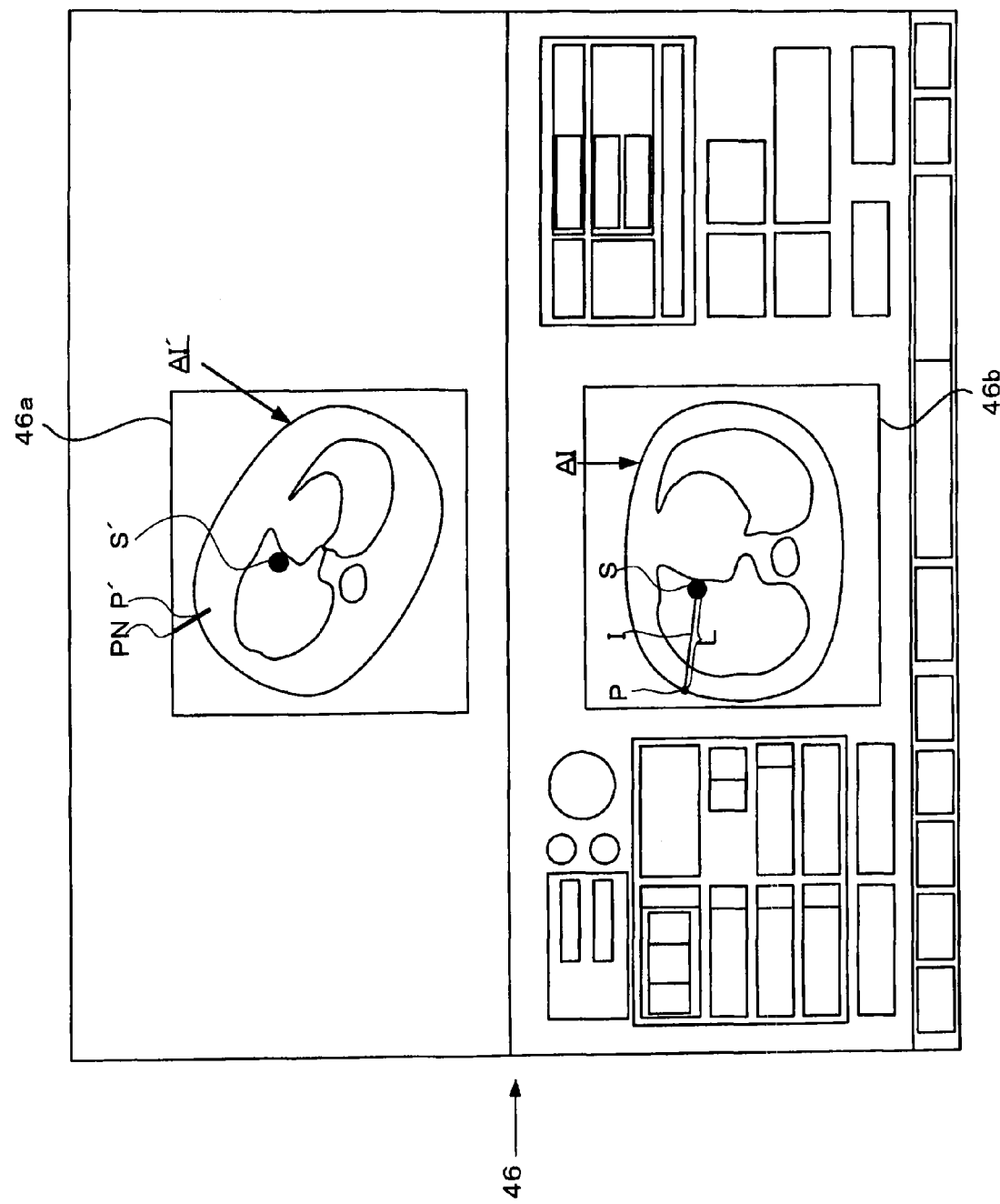
FIG. 7A is a diagram illustrating a screen of a display according to a modified example 1.
Figure 7B:
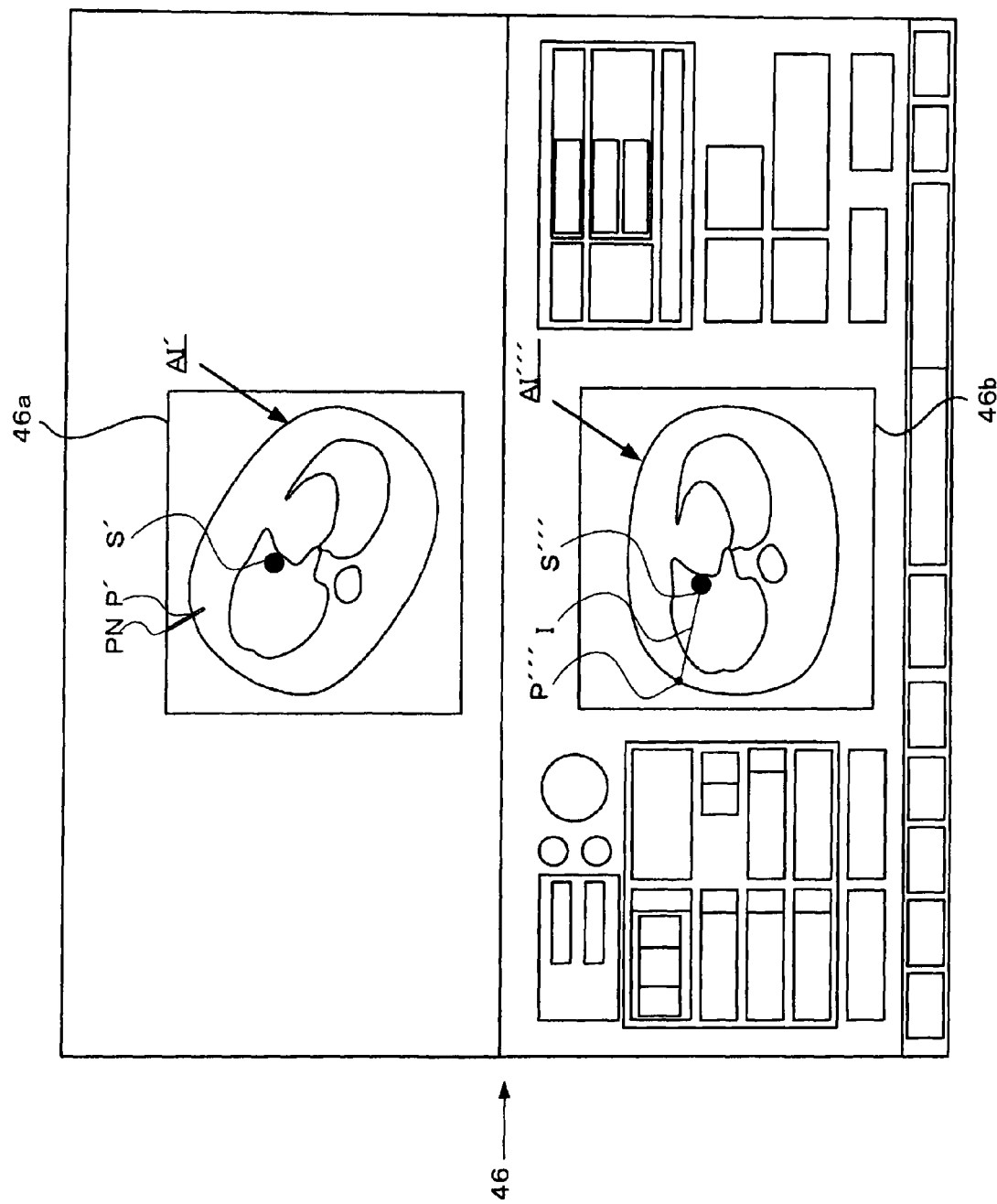
FIG. 7B is a diagram illustrating a screen of the display according to the modified example 1.

Hereinafter, the modified example is described with reference to FIG. 4A, FIG. 7A, and FIG. 7B. In the modified example, since the configurations are the same as those of the first embodiment apart from display modes of planned images and image processing methods for expressing the modes, the descriptions for the same parts as those of the first embodiment are omitted.

Firstly, creating a first planned image is the same as the present embodiment described above. The display screen 46b of the display 46, therefore, displays a first planned image AI based on first volume data as shown in FIG. 4A. Next, a second scanning is performed with respect to the subject E followed by creating a second axial image AI' based on second volume data. The second axial image AI' is displayed on the display screen 46a of the display 46 as shown in FIG. 7. In order to make the description of the modified example simple, the second axial image AI' is an image different from the first planned image AI. In fact, due to pulsation, the second axial image AI' based on the second volume data obtained from the second scanning may be different from the first planned image AI.

In the modified example, the displacement calculator 45 configuring the image processor 42 calculates displacement (transfer distance and rotational angel) between a position of a specific region in the second axial image AI' (for example, a position of a target site S' and an insert position P' of the puncture needle PN) (see FIG. 7A) and a position of a specific region in the first planned image AI, which is created in advance and includes the preliminarily created set image I and a first subject image HI (for example, a position of a target site S and an insert position P' of the puncture needle PN). A specific calculation method is similar to the one in the first embodiment above, so that the description thereof is omitted here.

The image transferring device 47 transfers (parallel transfers and rotational transfers) the second subject image in accordance with the calculated displacement, the image configuring the second axial image AI'. The image processor 42 creates the second planned image AI'" (see FIG. 7B) by drawing (superimposing and displaying) the set image I on a set position in the transferred second subject image, the position being set by the setter 43. The display controller 44 then replaces the first planned image AI with the created second planned image AI'", and allows the display 46 to display the replaced image AI' on the display screen 46a as a new planned image.

According to the modified example, since the second planned image is displayed, in place of the first planned image, as a new planned image, a latest planned image can be referred. A next planned image may also be created based on the new planned image.

Modified Example 2

Figure 8:
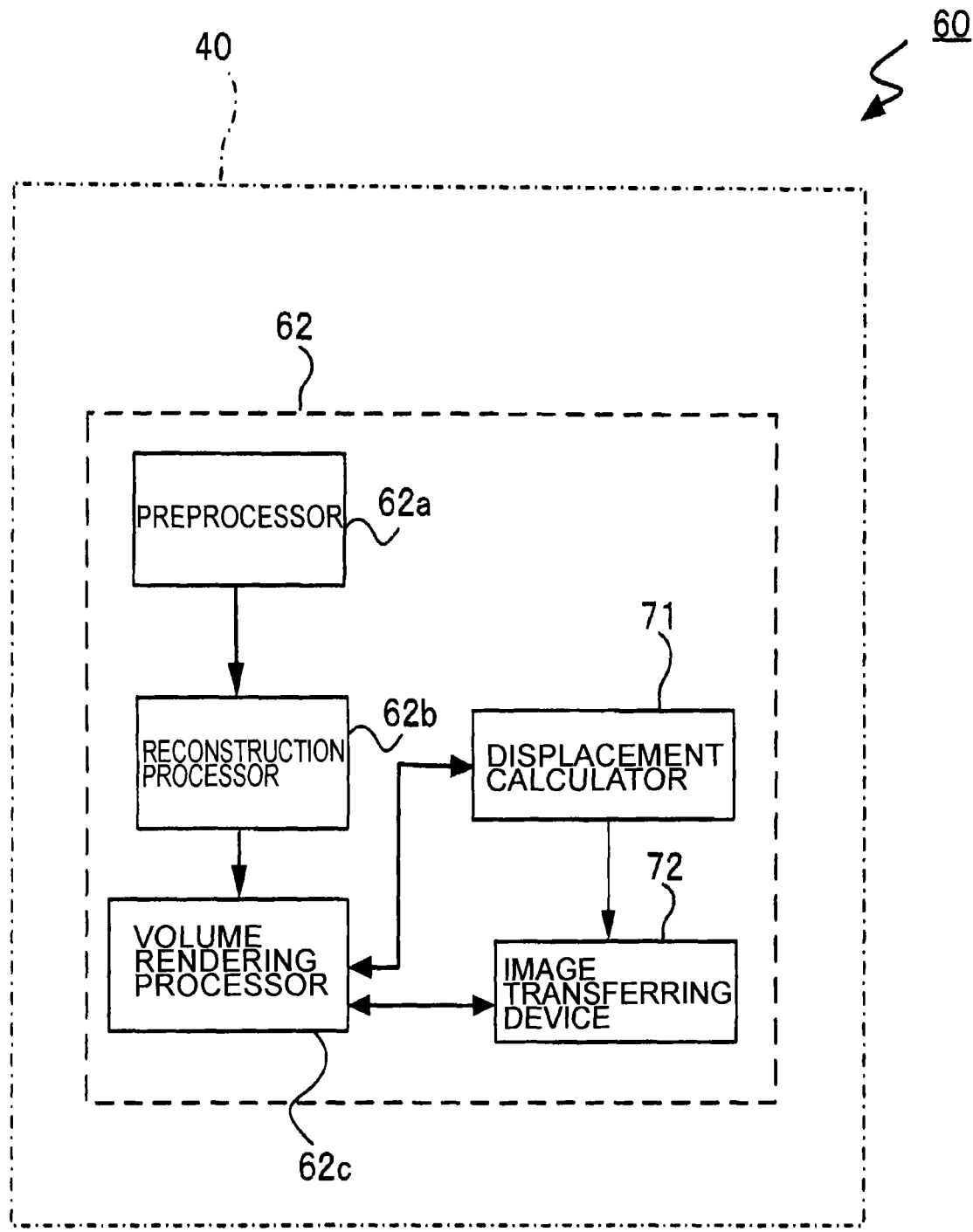
FIG. 8 is a block diagram illustrating an image processor, which configures an X-ray CT apparatus according to a modified example 2.

Next, a modified example 2 is described with reference to FIG. 8. An X-ray CT apparatus 60 according to a present modified example is configured to comprise a volume rendering processor 62c instead of the MPR rendering processor 42c in the first embodiment. Further, the detail descriptions of the configurations as same as those of the first embodiment are omitted.

The volume rendering processor 62c creates a three-dimensional image (image data) based on volume data. As a specific example, the volume rendering processor 62c creates a three-dimensional image of an image (image data) for display by performing a volume rendering process on volume data created by a reconstruction processor 62b.

The X-ray detector 12 detects X-rays transmitted through the subject E, and obtains detected data. The detected data detected by the X-ray detector 12 is acquired by the data acquisition system 18, and sent to an image processor 62 (preprocessor 62a).

The preprocessor 62a creates projection data with respect to the obtained detected data. The created projection data is sent to the reconstruction processor 62b based on the control of the controller 48.

The reconstruction processor 62b creates a plurality of tomographic image data based on the projection data created in S11 in FIG. 6. The reconstruction processor 62b also creates first volume data by performing an interpolate process on the plurality of tomographic image data.

The volume rendering processor 62c creates a three-dimensional image by performing the volume rendering process on the created first volume data. Next, in the three-dimensional image designated by the operator, a line segment connecting a position of a target site (lesion site) and an insert position of the puncture needle is set as a set image. The controller 44 then displays a three-dimensional image, which is the created three-dimensional image on which the preset set image is superimposed, as a first planned image (hereinafter, refers to as a "first three-dimensional planned image").

As referring to the three-dimensional image representing the set image, the operator starts performing a biopsy with respect to the subject E. After the biopsy is done to some extent, in order to verify a puncturing state, the X-ray CT apparatus 60 again performs X-ray scanning (second scanning) with respect to the subject E, then creates volume data (second volume data) based on the projection data.

The display controller 44 allows the display 46 to display the created three-dimensional image. Next, a displacement calculator 71 calculates displacement (transfer distance and rotational angel) between a position of a specific region in the three-dimensional image displayed on the display 46 (a target site position and an insert position of the puncture needle) and a position of a specific region in the first three-dimensional planned image including a preliminarily created subject image (cross section image of the subject) (a target site position and an insert position of the puncture needle). The displacement calculation method is the same as the one in the first embodiment above, so that the description thereof is omitted here.

Next, an image transferring device 72 transfers (parallel transfers and rotational transfers) only the set image in the first three-dimensional planned image, based on the calculated displacement. The set image after transferring is stored in the storage 49. The image processor 62 reads the set image after transferring out from the storage 49, and creates a second three-dimensional planned image by drawing the set image after transferring, which is previously read out, on the subject image in the three-dimensional image. The display controller 44 allows the display to display the second three-dimensional planned image, in place of the first three-dimensional planned image, as a new planned image.

In this way, when the position of the subject E is displaced, the display controller 44 can transfer the image (set image) of the insert passage of the puncture needle based on the displacement. The display controller 44 can also allow the display to display the image, which is the three-dimensional image on which the set image after transferring is drawn, as a new three-dimensional planned image. Thus, since no misalignment occurs between the three-dimensional image based on the second volume data and the new three-dimensional planned image after replacement, there is no chance for both images to be looked different.

Therefore, by referring to the replaced new three-dimensional planned image, image analysis of the three-dimensional image based on the second volume data becomes easier. That is, according to the present embodiment, it is possible to realize accuracy and efficiency in the puncturing work.

Second Embodiment

When a biopsy is performed with respect to a subject while displaying MPR images obtained by CT fluoroscopy, scanning and puncturing may be performed in alternative manner. Specifically, first, a MPR image of a subject is obtained by CT fluoroscopic. Doctors and the like are performed punctuation while referring to the MPR image. In this case, for example, in order to verify a position relationship between a puncture needlepoint and a body site from where a specimen is collected, the CT fluoroscopy is again performed when puncturing is done to some extent. The doctors and the like, further proceed transferring of the puncture needle towards the target site while referring to a MPR image obtained by the later CT fluoroscopy. The above operations are repeated until the biopsy is completed.

When such a repetitive work is performed, the puncture needlepoint may be displayed at vicinity of an edge of a screen. For example, when the puncture needlepoint is displayed at vicinity of an upper side edge of a screen, the lower region of the puncture needlepoint may be figured out; however, the upper region thereof may be difficult to figure out. Therefore, it is difficult to realize accuracy and efficiency in the puncturing work.

The present embodiment is to solve the above problem and the object is to provide an X-ray CT apparatus, which can realize accuracy and efficiency in the puncturing work.

Configurations of an X-ray CT apparatus 1 according to a second embodiment are described with reference to figures.

<Entire Configurations of X-Ray CT Apparatus 1>

Figure 9:
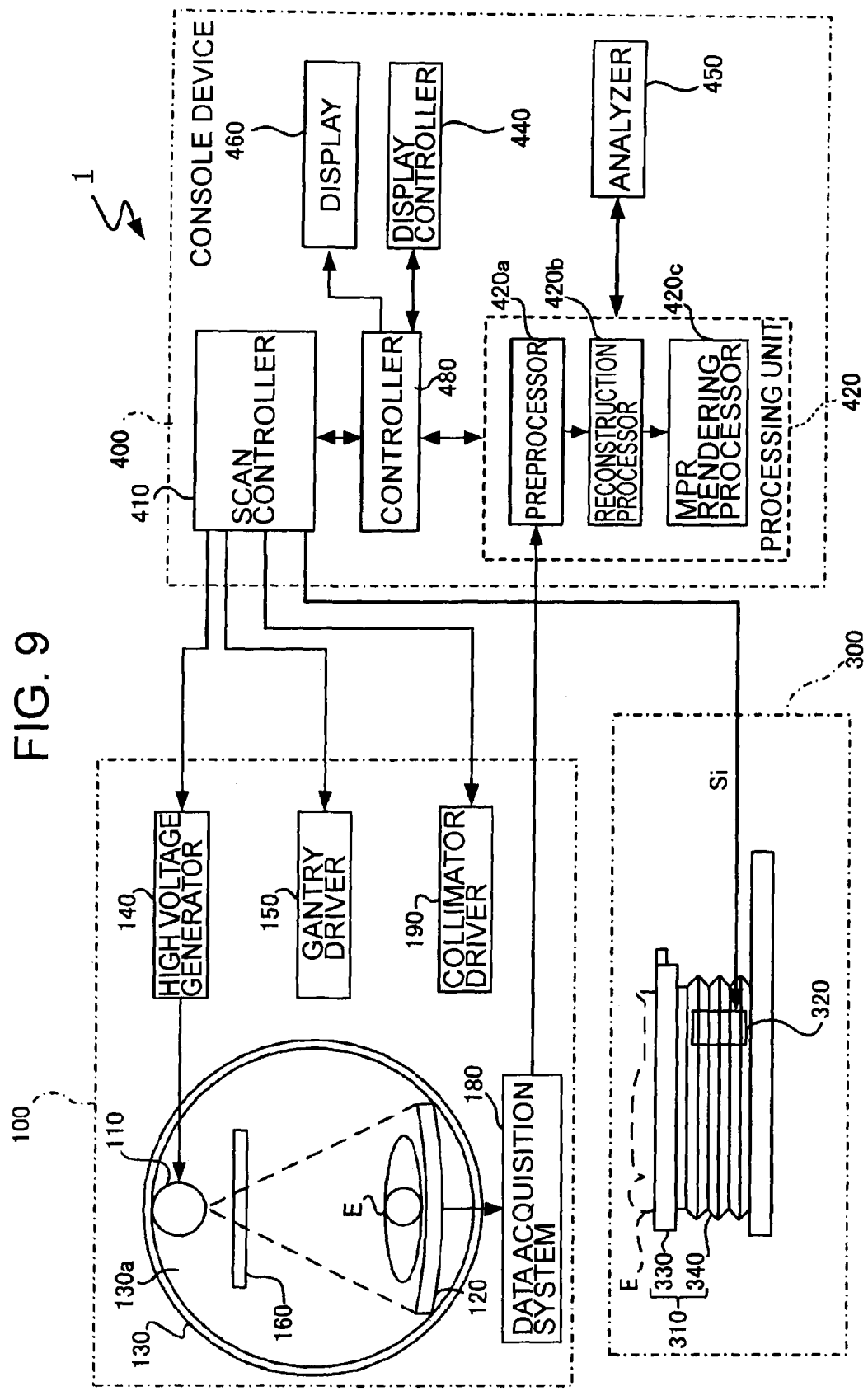
FIG. 9 is a block diagram of an X-ray CT apparatus according to a second embodiment.

As shown in FIG. 9, the X-ray CT apparatus 1 is configured to include a gantry apparatus 100, a couch apparatus 300, and a console device 400.

[Gantry Apparatus]

The gantry apparatus 100 is an apparatus, which exposes X-rays to a subject E and acquires detected data of the X-rays transmitted through the subject E. The gantry apparatus 100 comprises an X-ray generator 110, an X-ray detector 120, a rotating body 130, a high voltage generator 140, a gantry driver 150, an X-ray collimator device 160, a data acquisition system 180, and a collimator driver 190.

The X-ray generator 110 is configured to include an X-ray vacuum tube (for example, a conical or pyramid vacuum tube to generate beams. Not shown) to generate X-rays. The generated X-rays are exposed with respect to the subject E. The X-ray detector 120 is configured to include a plurality of X-ray detecting elements (not shown). The X-ray detector 120 detects X-ray intensity distribution data (detected data), which indicates intensity distribution of the X-rays transmitted through the subject E, with the X-ray detecting elements, and outputs the detected data as a current signal. As X-ray detector 12, for example, a two-dimensional X-ray detector (area detector) in which the plurality of detecting elements are arranged respectively in two directions (slice direction and channel direction) orthogonal to each other is used. The plurality of detecting elements, for example, three-hundred and twenty rows of those elements are provided along the slice direction. As descried above, by using an X-ray detector having multiple rows, a three-dimensional imaging domain having its width in the slice direction can be imaged by a single rotating scan. The slice direction corresponds to a rostrocaudal direction of the subject E, and the channel direction corresponds to a rotational direction of the X-ray generator 110.

The rotating body 130 is a member to support the X-ray generator 110 and the X-ray detector 120 facing to each other such that the subject E is sandwiched therebetween. The rotating body 130 includes an aperture 130a pierced through in the slice direction. In the gantry apparatus 100, the rotating body 130 is arranged to rotate around the subject E in a circular orbit.

The high voltage generator 140 applies high voltage to the X-ray generator 110. The X-ray generator 110 generates X-rays based on the high voltage.

The gantry driver 150 allows the rotating body 130 to rotate around the subject E based on a gantry drive control signal output from a scan controller 410. At this point, based on a transfer control signal output from the scan controller 410, the rotating body 130 transfers in the rostrocaudal direction (slice direction: z-axis direction), in the vertical direction (x-axis direction), and in the horizontal direction (y-axis direction) of the subject E. With the transferring of the rotating body 130, the X-ray generator 110 and the X-ray detector 120 both supported by the rotating body 130 are also transferred.

The X-ray collimator device 160 includes a slit (aperture) having a predetermined width, and adjusts a fan angle of the X-rays (angular spread of the X-rays in the channel direction) and a cone angle of the X-rays (angular spread of the X-rays in the slice direction) by changing the width of the slit, the X-ray being exposed from generator 110. The collimator driver 190 drives the X-ray collimator device 160 so that the X-rays generated from the X-ray generator 110 to be in a predetermined form.

The data acquisition system 180 (DAS) acquires the detected data from the X-ray detector 120 (each X-ray detecting element). The data acquisition system 18 also converts the acquired detected data (current signal) to a voltage signal, periodically integrates and amplifies the voltage signal, and converts the amplified voltage signal to the a digital signal. The data acquisition system 180 then sends the detected data, which is converted to the digital signal, to the console device 400 (a processor 420a (described later)). In a case when CT fluoroscopy is performed, based on the detected data acquired by the data acquisition system 180, it is desirable that a reconstruction processor 420b (described later) performs a reconstruction process in a short time and obtains a CT image in real time. Therefore, the data acquisition system 180 shortens the acquiring rate for the detected data.

[Couch Apparatus]

The couch apparatus 300 is an apparatus to place and transfer the subject E of an imaging target. The couch apparatus 300 comprises a couch 310, and a couch driver 320. The couch 310 comprises a couch top 330 for placing the subject E, and a base 340 for supporting the couch top 330. The couch top 330 can be transferred, in the rostrocaudal direction (back-and-forth direction: insertion-extraction direction with respect to the aperture 130a of the rotating body 130) and the horizontal direction (direction orthogonal to the rostrocaudal direction) of the subject E by the couch driver 320. The base 340 can transfer the couch top 330 in the vertical direction (direction orthogonal to the rostrocaudal direction) by the couch driver 320.

[Console Device]

The console device 400 is used for instruction input with respect to the X-ray CT apparatus 1. The console device 400 has functions such as reconstruction of CT image data (tomographic image data or volume data) representing internal morphology of the subject E from the detected data acquired from the gantry apparatus 100. The console device 400 is configured to include a scan controller 410, a processor 420, a display controller 440, an analyzer 450, a display 460, and a controller 480.

The scan controller 410, the processor 420, the analyzer 450, the display controller 440, and the controller 480 are configured from, for example, not shown processors such as CPU, GPU, and ASIC, and not shown storages such as ROM, RAM, and HDD. In the storage, control programs for executing functions of each device are stored. The processors such as CPU execute the functions of each device by executing each program stored in the storage.

The scan controller 410 controls a variety of operations related to X-ray scanning. For example, the scan controller 410 controls the high voltage generator 140 to apply high voltage to the X-ray generator 110. The scan controller 410 controls the gantry driver 150 to rotational drive the rotating body 130. The scan controller 410 controls the collimator driver 190 to operate the X-ray collimator device 160. The scan controller 41 also controls the couch driver 320 to transfer the couch top 330.

The processor 420 executes a variety of processes on the detected data sent from the gantry apparatus 100 (data acquisition system 180). The processor 420 is configured to include a preprocessor 420a, a reconstruction processor 420b, and a MPR rendering processor 420c.

The preprocessor 420a performs preprocessing such as a logarithmic conversion process, offset correction, sensitivity correction, beam hardening correction, with respect to the detected data detected by the gantry apparatus 100 (X-ray detector 120), and creates projection data (row data).

The reconstruction processor 420b creates CT image data (tomographic image data or volume data) based on the projection data created by the preprocessor 420a. For reconstructing of the tomographic image data, for example, an arbitrary method may be used, the method including the two-dimensional Fourier transform method, the Convolution-Backprojection method, and the like. The volume data is created by performing an interpolate process on the plurality of reconstructed tomographic image data. For reconstructing of the volume data, for example, an arbitrary method may be used, the method including a cone-beam reconstruction method, a multi-slice reconstruction method, an enlarge reconstruction method, and the like. Reconstruction of extensive volume data can be achieved by volume scanning using the X-ray detector having multiple rows described as above.

The MPR rendering processor 420c creates a plurality of MPR images (axial image, sagittal image, and coronal image of three orthogonal cross sections) by rendering the volume data, which is previously created (reconstructed) by the reconstruction processor 420b, in an arbitrary direction.

Figure 10A:
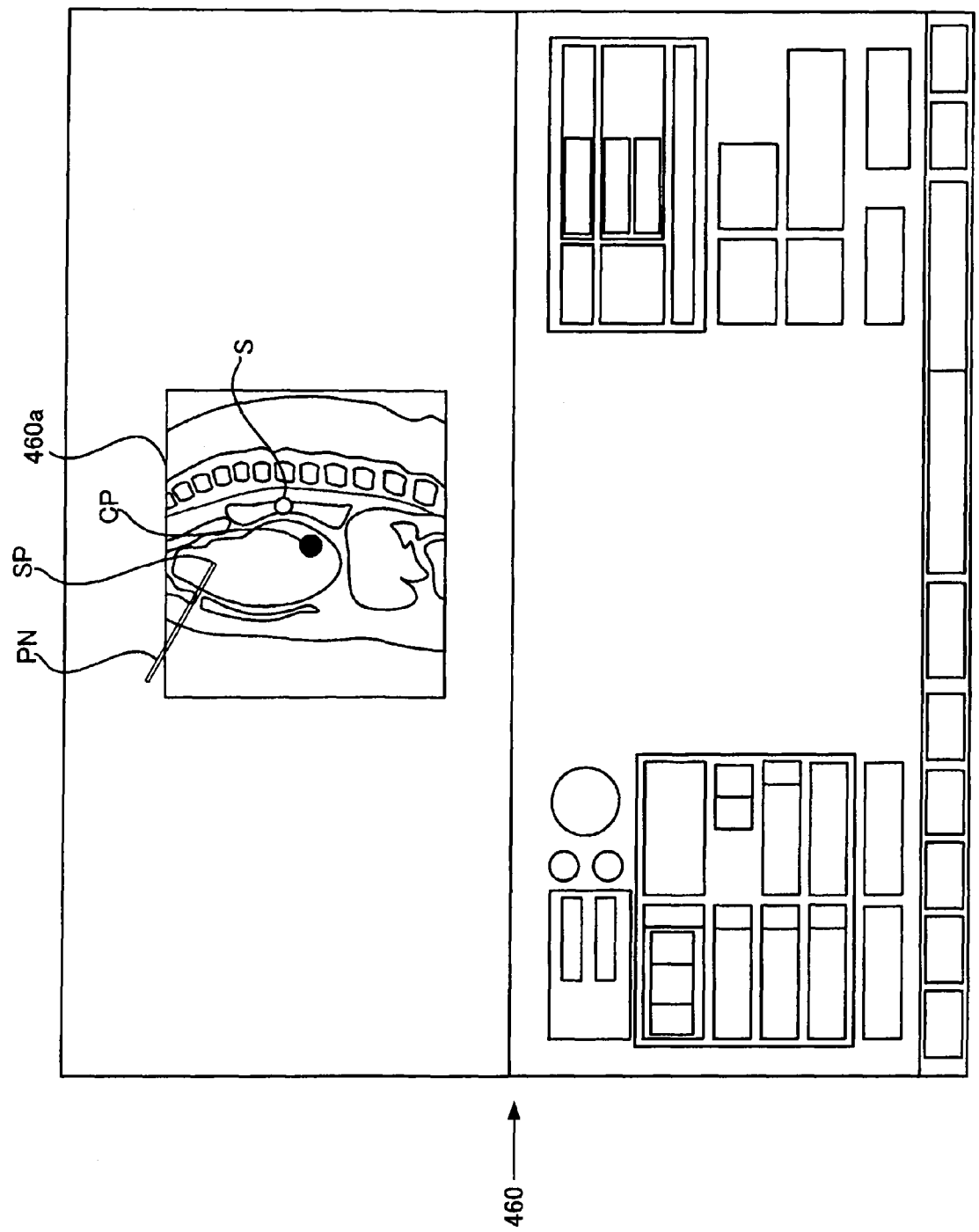
FIG. 10A is a diagram illustrating a screen of a display according to the second embodiment.
Figure 10B:
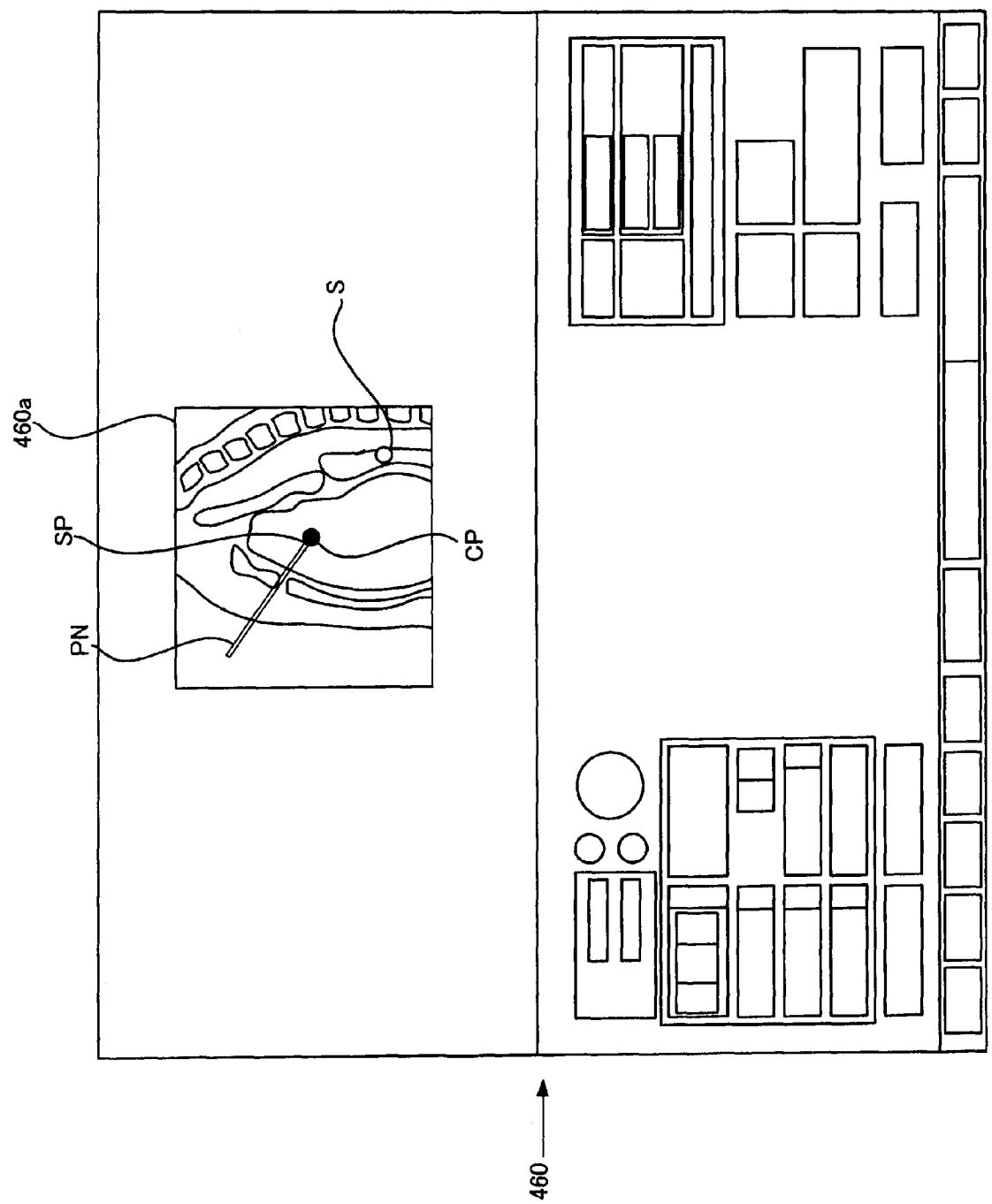
FIG. 10B is a diagram illustrating a screen of the display according to the second embodiment.
Figure 12A:
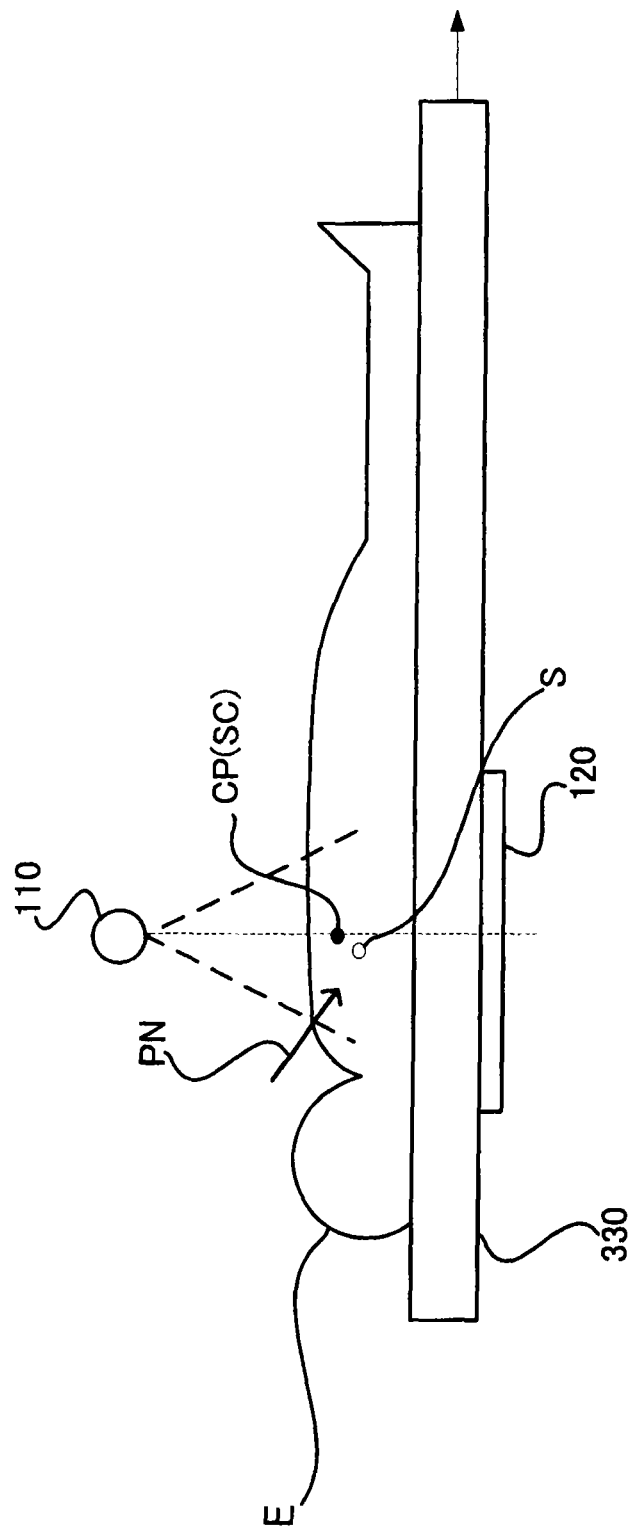
FIG. 12A is a schematic diagram illustrating a relationship between a central position of scanning and a needlepoint position, before a couch top is transferred.
Figure 12B:
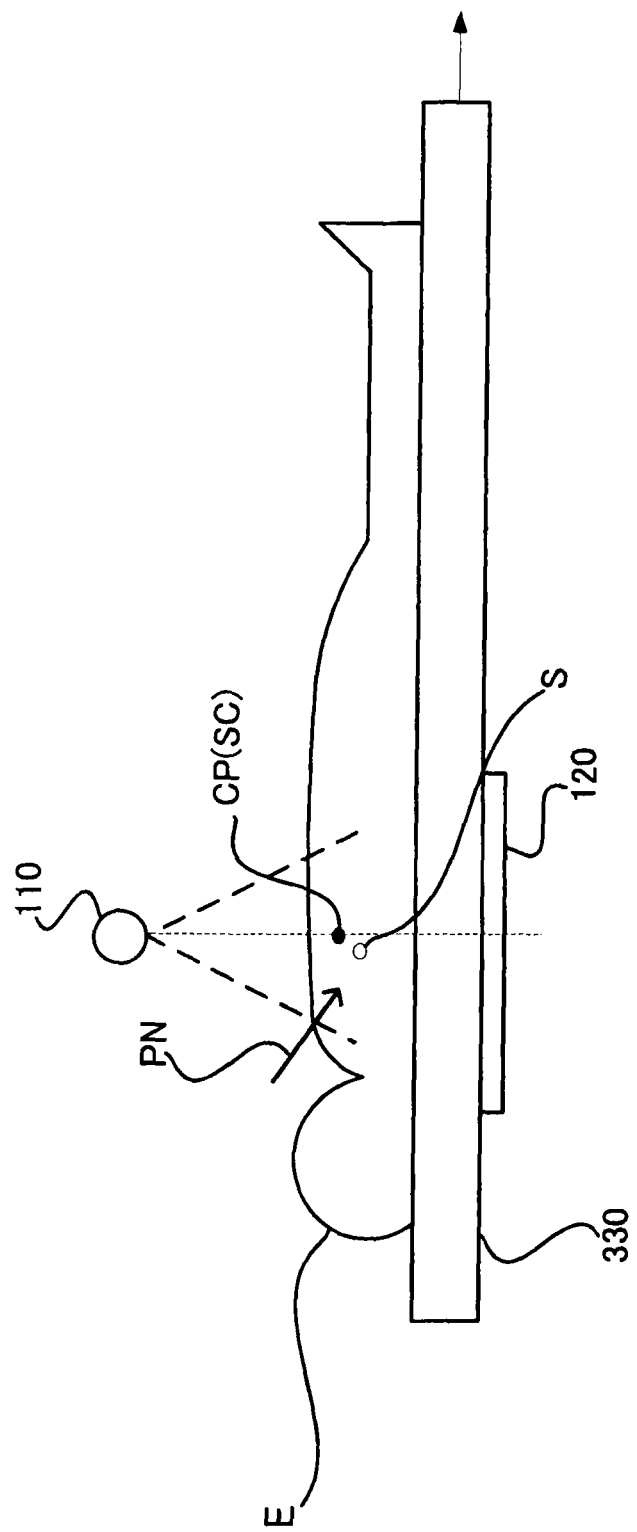
FIG. 12B is a schematic diagram illustrating a relationship between a central position of scanning and a needlepoint position, after the couch top is transferred.

In the present embodiment, the sagittal image created by the MPR rendering processor 420b is displayed on a display screen 460a of the display 460 (see FIG. 10A and FIG. 10B). In FIG. 10A and FIG. 10B, the example displaying the sagittal image is shown; however, an axial image, or a coronal image may be displayed.

Further, the MPR rendering processor 420c can create an oblique image, which is an image of any arbitrary cross section of the volume data, as a MPR image. For example, draw a line segment where a cross section is desired in a MPR image displayed on the display 460. The MPR rendering processor 420c creates an oblique image by rendering the volume data in a predetermined direction using the line segment as a reference.

The display controller 44 controls a variety of controls for image display. For example, the display controller 440 controls the display 460 to display the MPR image (sagittal image in the example in FIG. 10A and FIG. 10B) created by the MPR processor 420c.

The analyzer 450 is configured to include an identifying device 510, a displacement calculator 520, and a transfer amount determinator 530.

The identifying device 510 identifies the MPR image, on which a later described needlepoint SP is displayed, from the plurality of MPR images, identifies a position the needlepoint SP of the puncture needle in the identified image (hereinafter, refers to as a "needlepoint position SP"), and designates the identified needlepoint poison SP as a needlepoint position in the image region. When a MPR image, on which the needlepoint is displayed, is identified from the plurality of the MPR images (a MPR image in the identified region), for example, the MPR image in the identified region can be identified by the identifying device 510 by taking a difference between adjacent MPR images.

Specifically, the identifying device 510 takes a difference between the MPR images, identifies a MPR image having a large difference, performs an image process such as edge detection with respect to the identified MPR image, and identifies the MPR image in the identified region. The identifying device 510 designates the identified MPR image as the MPR image, on which the needlepoint is displayed.

Next, the identifying device 510 compares a luminance value of pixels configuring the designated MPR image with a preliminary set threshold value, and identifies coordinate values of the pixels larger (or smaller) than the threshold value as the needlepoint position SP of the puncture needle. Here, the threshold value is a luminance value, which is preliminary set, corresponds to the needlepoint of the puncture needle, and is to determine whether the needlepoint of the puncture needle is included in the pixels.

Next, the identifying device 510 designates the coordinate values of the identified pixels as the needlepoint position SP of the puncture needle in the image region. In this way, the needlepoint position SP is automatically designated by the identifying device 510.

[Displacement Calculator]

Hereinafter, operations of the displacement calculator are described with reference to FIG. 12A, FIG. 12B, FIG. 13A, FIG. 13B, FIG. 14A, and FIG. 14B.

The displacement calculator 520 calculates displacement between a position of the needlepoint SP of the designated puncture needle PN and a position of a center CP of the MPR image. The displacement is, specifically, as shown in FIG. 14A and FIG. 14B, obtained by taking a difference (X2−X1, Y2−Y1, Z2−Z1) between coordinate values (X1, Y1, Z1) of the needlepoint SP and coordinate values (X2, Y2, Z2) of the center CP of the MPR image. The above description, however, is based on the premise that, on a same coordinate, a MPR image center CP is coincided with a scanning center SC. As described above, the displacement is derived from taking a difference between the coordinate values of the needlepoint SP and the coordinate values of the MPR image center CP (Displace from FIG. 12A to FIG. 12B, displace from FIG. 13A to FIG. 13B, and displace from FIG. 14A to FIG. 14B).

The transfer amount determinator 530 determines a relative transfer amount of the couch top 330 and the gantry apparatus 100 corresponding to the displacement obtained by the displacement calculator 520. The transfer amount is obtained by converting the earlier displacement into displacement in a real coordinate. For example, displacement of 50 pixels will be the transfer amount of 25 mm in the real coordinates.

In addition, in the present embodiment, in the volume data obtained by scanning, the display controller 440 allows the display 460 to display the MPR image having a cross section of the position in the image region stored in the storage 450.

The controller 480 performs a total control of the X-ray CT apparatus 1 by controlling the operations of the gantry apparatus 100, the couch apparatus 300, and the console device 400. For example, the controller 480 controls the scan controller 410 to allow execution of preliminarily scanning and main scanning with respect to the gantry apparatus 100 and acquisition of the detected data. The controller 480 also controls the processor 420 to allow execution of various processes (preliminarily process, reconstruction process, MPR process, and the like) with respect to the detected data. Alternatively, the controller 480 controls the display controller 440 to allows the display 460 to display a CT image based on the image data created by the processor 420.

<Operations>

Figure 14B:
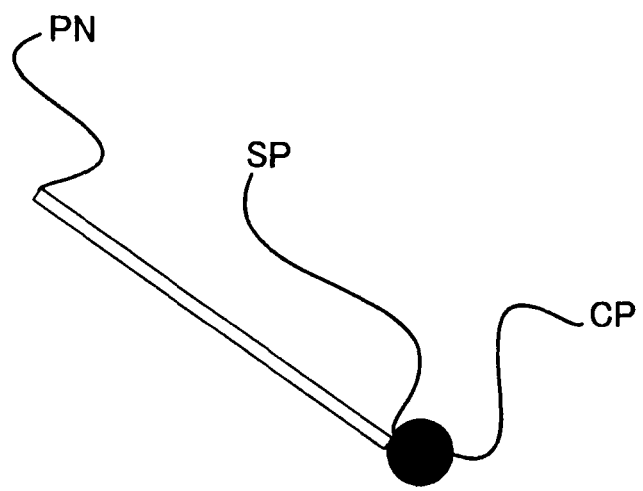
FIG. 14B is a diagram for describing the difference between the coordinates of the needlepoint and the coordinates of the center of scanning on the MPR image.
Figure 15:
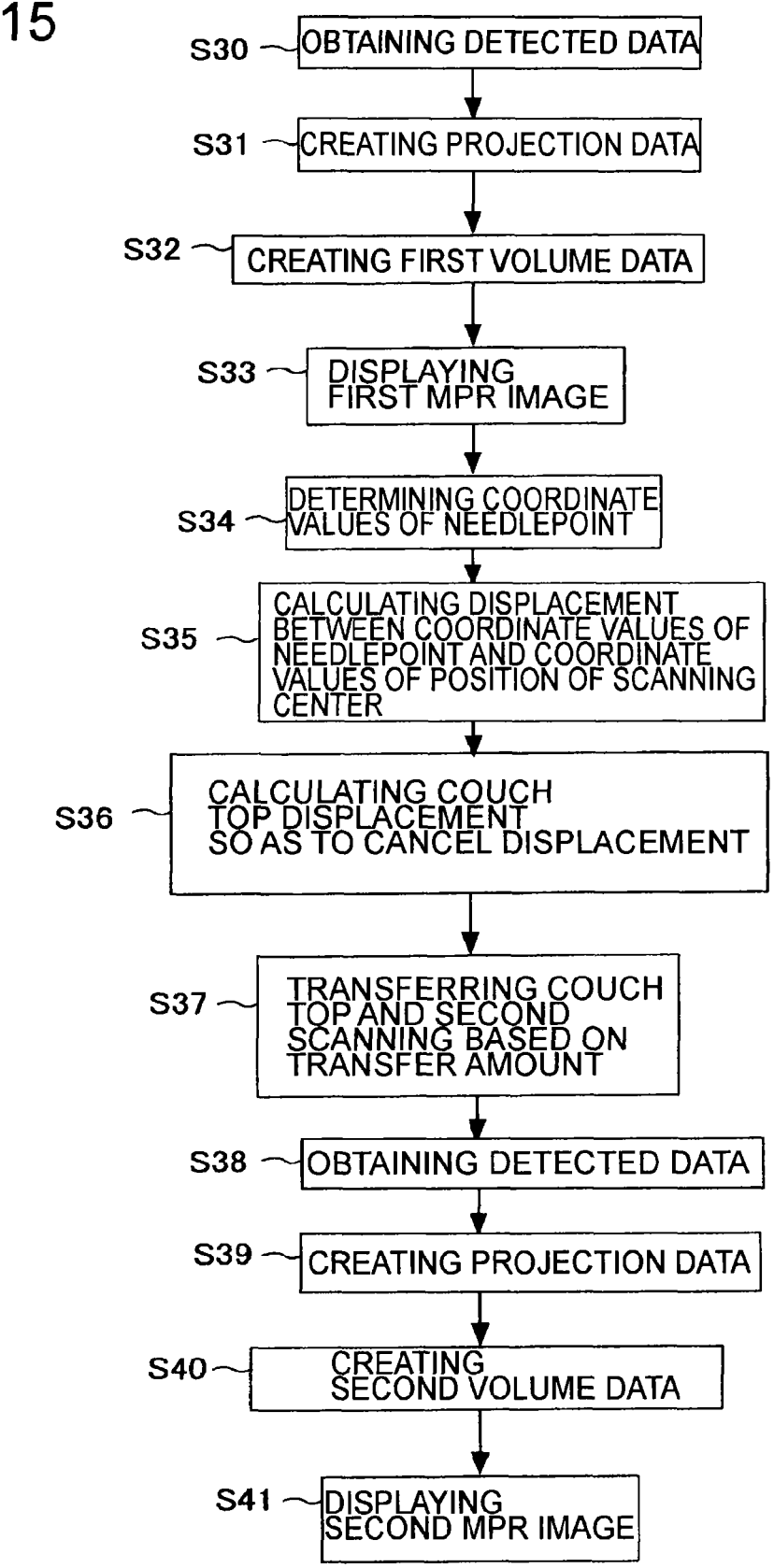
FIG. 15 is a flowchart illustrating an operation outline of the X-ray CT apparatus according to the second embodiment.

Hereinafter, as referring to FIG. 15, operations of the X-ray CT apparatus 1 according to the present embodiment are described. Here, operations are described in a case such that CT fluoroscopic and puncturing are performed in alternative manner and a subject S of a biopsy (see FIG. 10A, FIG. 10B, FIG. 12A, FIG. 12B, FIG. 13A, FIG. 13B, FIG. 14A, and FIG. 14B) is punctured with a puncture needle PN.

In starting puncturing, first, the X-ray CT apparatus 1 performs X-ray scanning with respect to a subject E, and creates a first volume data.

Specifically, the X-ray generator 110 exposes X-rays with respect to the subject E. The X-ray detector 120 detects the X-rays transmitted through the subject E, and obtains detected data (S30). The detected data in one-roll is obtained in the present embodiment. The detected data detected by the X-ray detector 120 is acquired by the data acquiring system 180, and sent to the processor 420 (preprocessor 420a).

The preprocessor 420a performs preprocessing with respect to the detected data obtained in S30, and creates projection data (S31). The created projection data is sent to the reconstruction processor 420b based on the control of the controller 480.

The reconstruction processor 420b creates a plurality of tomographic image data based on the projection data created in S31. The reconstruction processor 420b then creates a first volume data by performing an interpolate process on the plurality of tomographic image data (S32).

The MPR rendering processor 420c creates a plurality of MPR images by rendering the first volume data, which is created in S32, in an arbitrary direction. The identifying device 510 designates a first MPR image, on which the needlepoint of the puncture needle is displayed, from the plurality of MPR images.

The MPR rendering processor 420c creates MPR images of three orthogonal cross sections (axial image, sagittal image, and coronal image) in the designated first MPR image. In the present embodiment, a sagittal image is created as the MPR image, and the created sagittal image is displayed as the first MPR image on the display 460 by the display controller 440.

Next, the identifying device 510 determines coordinate values of the needlepoint of the puncture needle (S34). The displacement calculator 520 then calculates displacement of the coordinate values (X1, Y1, Z1) of the needlepoint of the designated puncture needle and coordinate values (X2, Y2, Z2) of a position of a scanning center SC (MPR image center CP) (S35).

That is, as mentioned earlier, since the description is based on the premise that, on a same coordinate, a MPR image center CP is coincided with a scanning center SC, the displacement calculator 520 determines displacement (X2−X1, Y2−Y1, Z2−Z1) between the needlepoint position SP (X1, Y1, Z1) of the designated puncture needle PN and the centre CP (X2, Y2, Z2) of the MPR image. The transfer amount determinator 530 calculates a relative transfer amount of the couch top 330 and the gantry apparatus 100 corresponding to the displacement, so as to cancel the calculated displacement (make the position of the scanning center SC (hereinafter, refers to as a "scanning center position SC") coincide with the coordinate value of the needlepoint SP of the puncture needle). In the present embodiment, a transfer amount of the couch top 330 is calculated (S36).

A second scan starting signal (not shown) including the transfer amount is then sent to the scan controller 410. The relative transfer amount is a difference between real coordinate values of the couch top 330 and the gantry apparatus 100 before and after transferring. The information of the transfer amount is sent to the scan controller 410 as new real coordinate values of the couch top 330 and the gantry apparatus 100 after transferring.

Patterns of relative transferring of the couch top 330 and the gantry apparatus 100 include such as a case when only the couch top 330 is transferred, a case when only the gantry apparatus 100 is transferred, and a case when both the couch top 330 and the gantry apparatus 100 are transferred. In the present embodiment, it is described the case when only the couch top 330 is transferred based on the determined transfer amount.

The scan controller 410 sends a transfer control signal Si (see FIG. 9) to the couch top 330 to transfer the couch top 330 by only the determined transfer amount. Upon receiving the transfer control signal Si, the couch top 330 is transferred by only the determined transfer amount by vertical transferring, back-and-forth transferring, and/or horizontal transferring. The scan controller 410 then performs X-ray scanning (second scanning) with respect to the subject E (S37).

The X-ray detector 120 detects the X-ray exposed with respect to the subject E, and obtains detected data (S38). The detected data detected by the X-ray detector 120 is acquired by the data acquiring system 180, and sent to the processor 420 (preprocessor 420a).

The preprocessor 420a performs preprocessing with respect to the detected data obtained in S38, and creates projection data (S39). The created projection data is sent to the reconstruction processor 420b based on the control of the controller 480.

The reconstruction processor 420b creates a plurality of tomographic image data based on the projection data created in S39. The reconstruction processor 420b also creates a second volume data by performing an interpolate process on the plurality of tomographic image data (S40).

The MPR rendering processor 420c creates a plurality of MPR images by rendering the second volume data, which is created in S40, in an arbitrary direction. The identifying device 510 designates a second MPR image, on which the needlepoint of the puncture needle is displayed, from the plurality of MPR images. Further, the designation is automatically designated based on the designation information when the first MPR image is designated in S33.

In the present embodiment, the MPR rendering processor 420c creates MPR images of three orthogonal cross sections (axial image, sagittal image, and coronal image) in the designated second MPR image. The created second MPR image is displayed on the display 460 by the display controller 440 (S41. See FIG. 10B). As it can be seen from looking at the second MPR image displayed on the display 460, it is displayed a MPR image, in which the needlepoint position SP of the puncture needle and the scanning center position SC are coincident, in the second MPR image (see FIG. 10B, FIG. 12B, FIG. 13B, and FIG. 14B).

Hereinafter, in order to verify misalignment between the needlepoint position SP of the puncture needle and the scanning center position SC when puncturing is done to some extent, the X-ray apparatus 1 again performs X-ray scanning (third scanning) with respect to the subject E, creates volume data (third volume data), and repeats the processes from S30 till S41.

<Effect>

The X-ray CT apparatus 1 of the present embodiment is an apparatus to create volume data based on a result obtained by X-ray scanning of a subject E for medical practice with a puncture needle PN. The X-ray CT apparatus 1 comprises the MPR rendering processor 420c, the identifying device 510, the displacement calculator 520, the scan controller 410, and the display controller 440. The MPR rendering processor 420c creates a first MPR image in which the puncture needle PN is drawn based on first volume data obtained by a first scanning. The identifying device 510 identifies a position of a needlepoint SP of the puncture needle PN in the first MPR image created. The displacement calculator 520 determines displacement between the identified needlepoint position SP and a center CP of the first MPR image. The scan controller 410 performs a second scanning by displacing the scanning center of the first scanning so as to cancel the earlier displacement. The display controller 440 allows the display 460 to display a second MPR image, which is created by the MPR rendering processor 420c based on second volume data obtained by the second scanning and is in the same cross section as the first MPR image.

Specifically, the X-ray CT apparatus 1 comprises the couch top 330, on which the subject E is placed, and the gantry apparatus 100, which performs scanning. Based on the displacement, the X-ray CT apparatus comprises the transfer amount determinator 530 determining a transfer amount of a relative position between the couch top 330 and the gantry apparatus 100. The scan controller 410 controls transferring of the couch top 330 and/or the gantry apparatus 100, in accordance with the designated transfer amount.

Figure 13A:
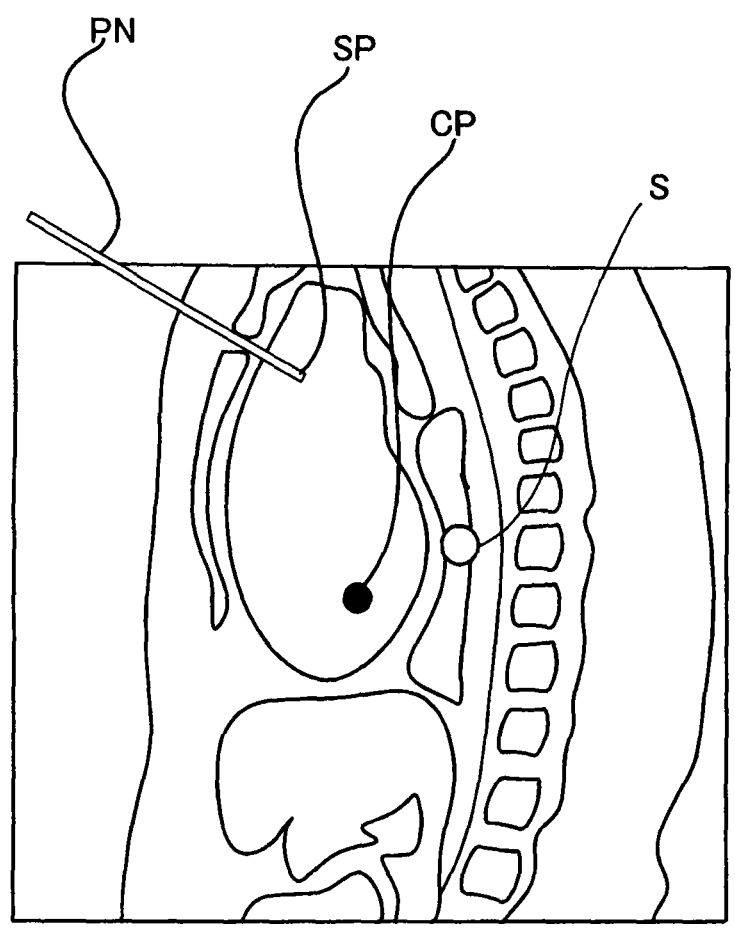
FIG. 13A is a diagram illustrating a first MPR image drawn on a screen.
Figure 13B:
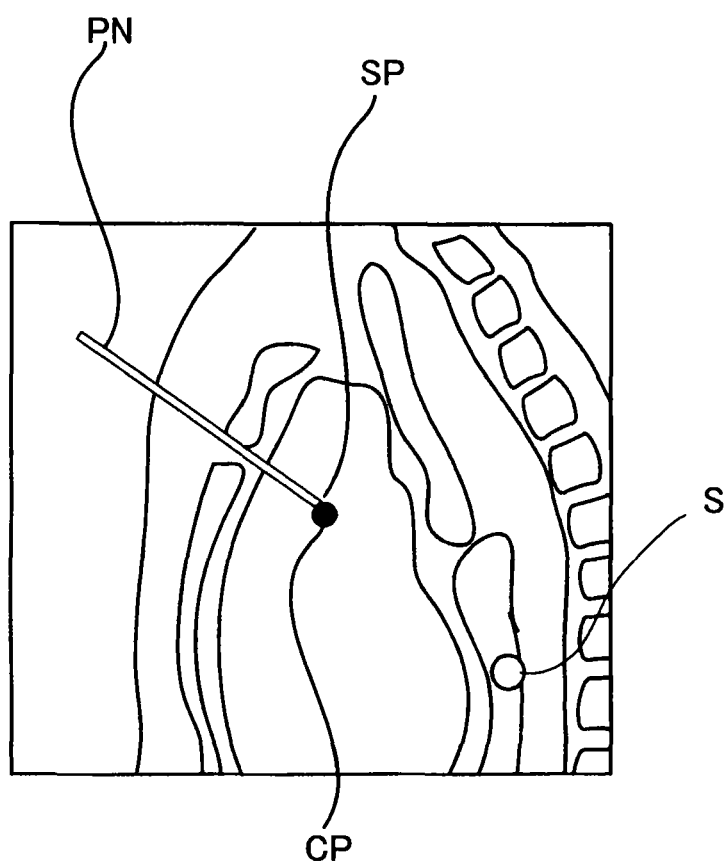
FIG. 13B is a diagram illustrating a second MPR image drawn on a screen.

Thus, as shown in FIG. 13A and FIG. 13B, since the needlepoint SP of the puncture needle PN can always be displayed at the center of the display screen 460a, a complete view of a region around the puncture needle PN can be precisely obtained. It is therefore possible to realize accuracy and efficiency in the puncturing work.

Modified Example 3

In the above embodiment, as a pattern of relative transferring of the couch top 330 and the gantry apparatus 100, it has been described the case when only the couch top 330 is transferred. However, hereinafter, the case when only the gantry apparatus 100 is transferred and the case when both the couch top 330 and the gantry apparatus 100 are transferred are described.

Transferring of the gantry apparatus 100 includes transferring by tilting a gantry in addition to vertical transferring, horizontal transferring, and back and forth transferring. Vertical transferring, horizontal transferring and back and forth transferring may be determined in the same way as the case of the couch top 330. When a gantry is tilted, coordinates of the gantry before tilting (before rotation) and coordinates of the gantry after tilting (after rotation) are mapped using a rotation matrix of three-dimensional polar coordinates. Here, the coordinates of the needlepoint of the puncture needle and the coordinates of the scanning center are already known, a tilt angel is obtained by determining an inverse matrix of the above rotation matrix.

As described above, transferring amount of the gantry apparatus 100 is determined based on the displacement of the coordinates of the needlepoint of the puncture needle and the coordinates of the scanning center. In the case when both the couch top 330 and the gantry apparatus 100 are transferred, transferring amount is relatively determined by a combination of the above method in which only the couch top 330 is transferred and the method in which only the gantry apparatus 100 is transferred.

Third Embodiment

Figure 16:
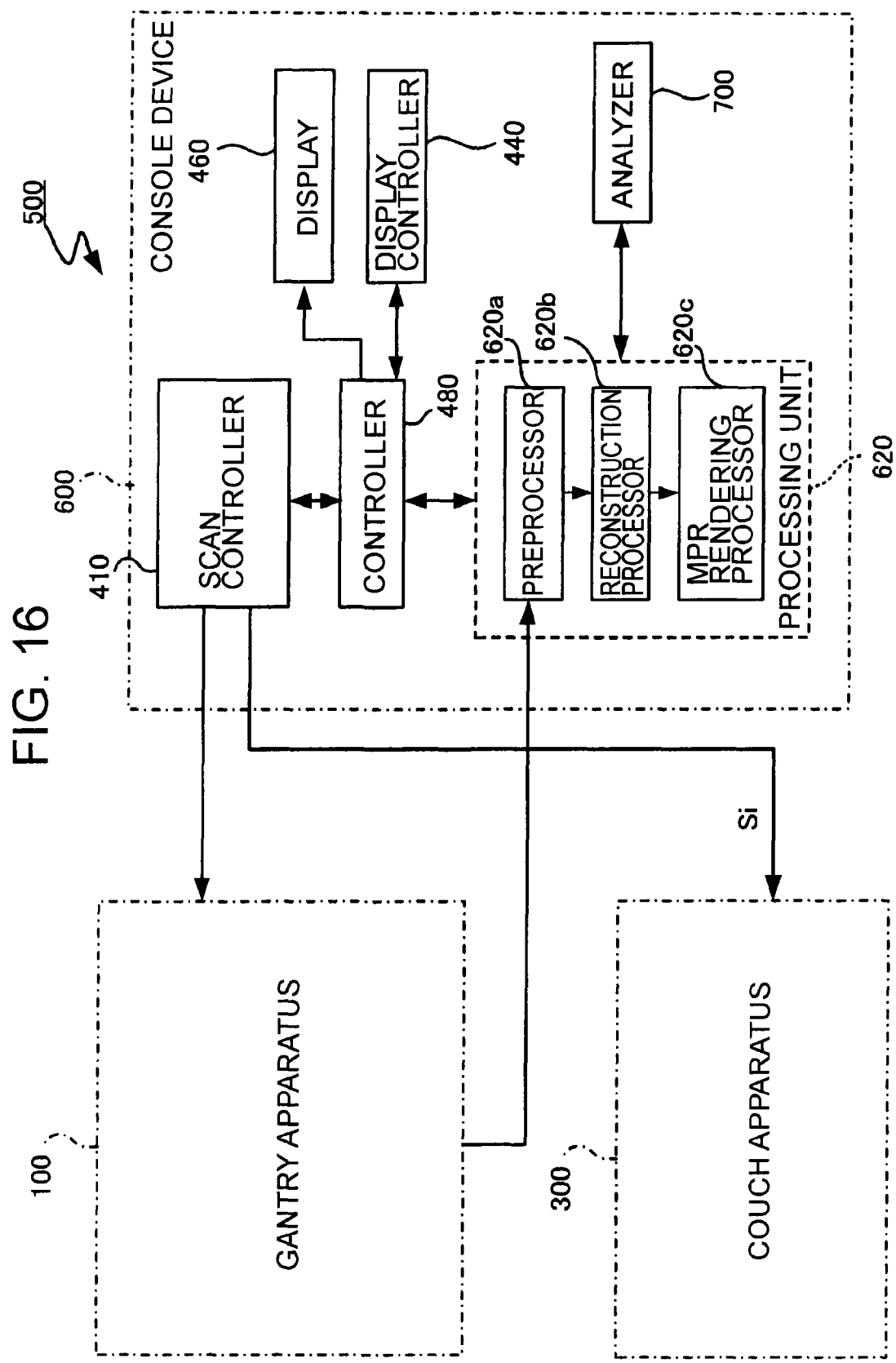
FIG. 16 is a block diagram illustrating an X-ray CT apparatus according to a third embodiment.
Figure 17:
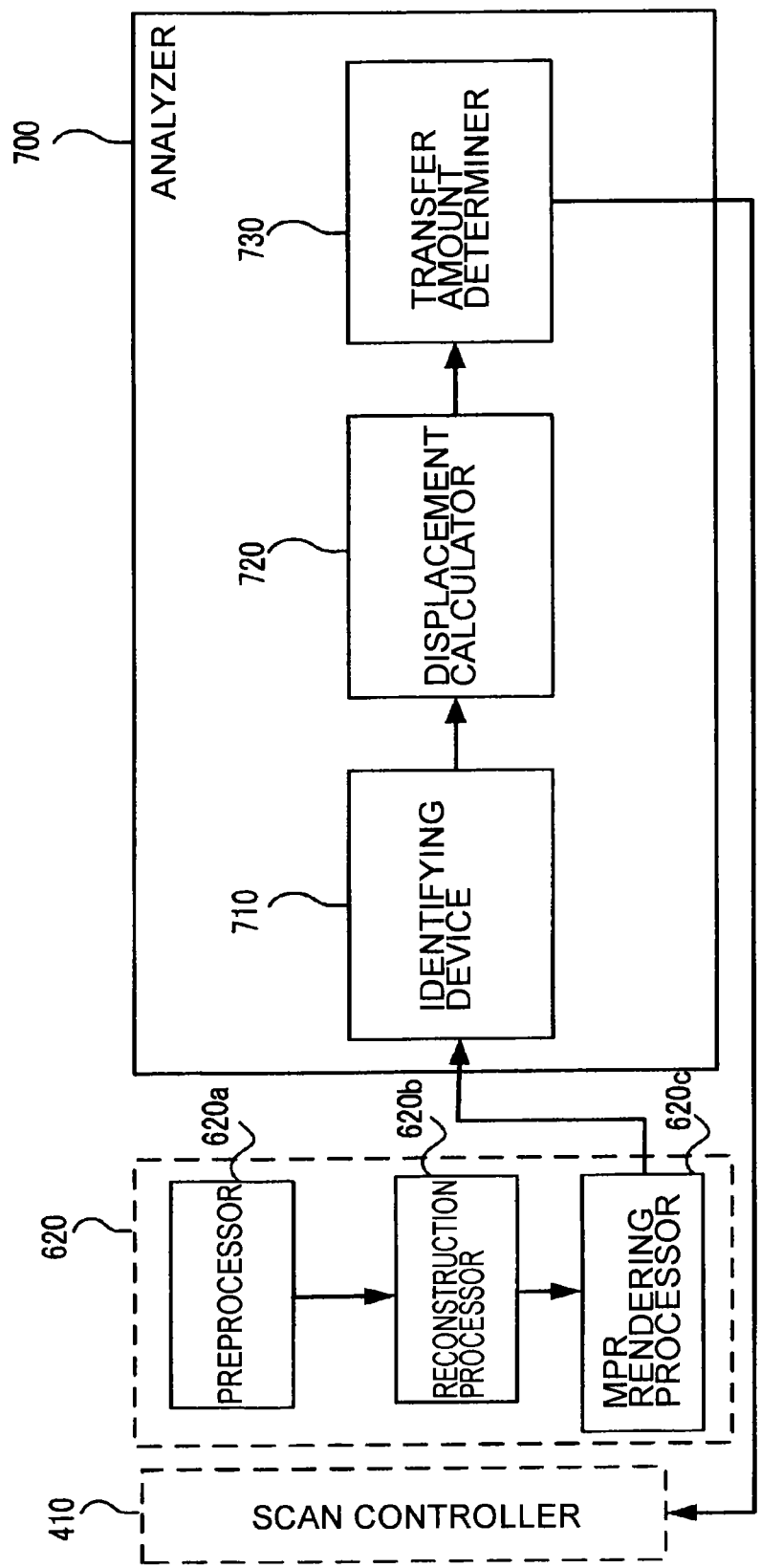
FIG. 17 is a block diagram illustrating configurations of an analyzer according to the third embodiment.

Next, as referring to FIG. 16 and FIG. 17, configurations of an X-ray CT apparatus 500 according to a third embodiment are described. The X-ray CT apparatus 500 of the present invention automatically designates a needlepoint position SP of a puncture needle based on volume data, and performs a second scanning by displacing the scanning center of a first scanning so as to cancel the displacement of the needlepoint position SP of the puncture needle and a scanning center position SC. The configurations are the same as those of the second embodiment above except comprising a processor 620 and an analyzer 700, so that the detail descriptions thereof may be omitted.

<Entire Configurations of X-Ray CT Apparatus 500>

As shown in FIG. 16, the X-ray CT apparatus 500 is configured to include a gantry apparatus 100, a couch apparatus 300, and a console device 600.

<Console Device>

The console device 600 is configured to include a scan controller 410, a processor 620, a display controller 440, a display 460, a controller 480, and an analyzer 700. The processor 620 executes a variety of processes on detected data sent from the gantry apparatus 100 (data acquisition system 180). The processor 620 is configured to include a preprocessor 620*a*, a reconstruction processor 620*b*, and a volume rendering processor 620*c*.

The volume rendering processor 620*c* creates a three-dimensional image based on volume data created by the reconstruction processor 620*b*. Specifically, the volume rendering processor 620*c* creates a first three-dimensional image by performing ray tracing with respect to the created volume data, determining brightness at each voxel (CT value), projecting image information based on the brightness onto pixels on a projection plane, and sterically-extracting internal organs, and the like to create a three-dimensional image The three-dimensional image is displayed on the display 460 by the display controller 440.

The analyzer 700 is configured with, as shown in FIG. 17, an identifying device 710, a displacement calculator 720, and a transfer amount determinator 730. The identifying device 710 identifies a needlepoint position based on the three-dimensional image, on which a puncture needle PN is drawn, created based on the volume data. Next, the identifying device 710 designates the identified needlepoint position SP as a needlepoint position in a display image region of the display 460.

The identifying device 710 compares the CT values of each voxel configuring the volume data with a preliminary set threshold value, and identifies coordinate values of the voxel having the CT value larger (or smaller) than the threshold value as the needlepoint position SP of the puncture needle. Here, the threshold value is a CT value, which is preliminary set and corresponds to materials (for example, metal) of the puncture needle, to determine whether the needlepoint of the puncture needle is included in the voxels. Next, the identifying device 710 designates the coordinate values of the identified voxel in the image region as the needlepoint position SP of the puncture needle. In this way, the needlepoint position SP is automatically designated by the identifying device 710.

[Displacement Calculator]

Figure 18A:
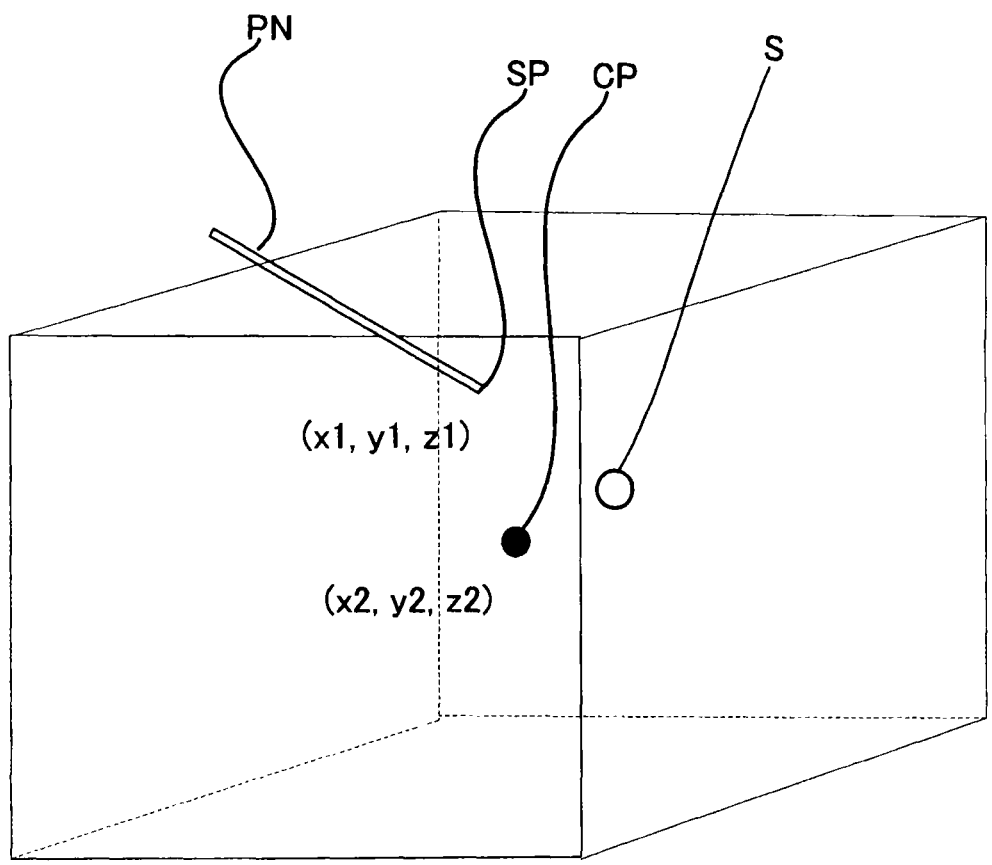
FIG. 18A is a diagram for describing a difference between coordinates of a needlepoint and coordinates of a center of scanning on a three-dimensional image.
Figure 18B:
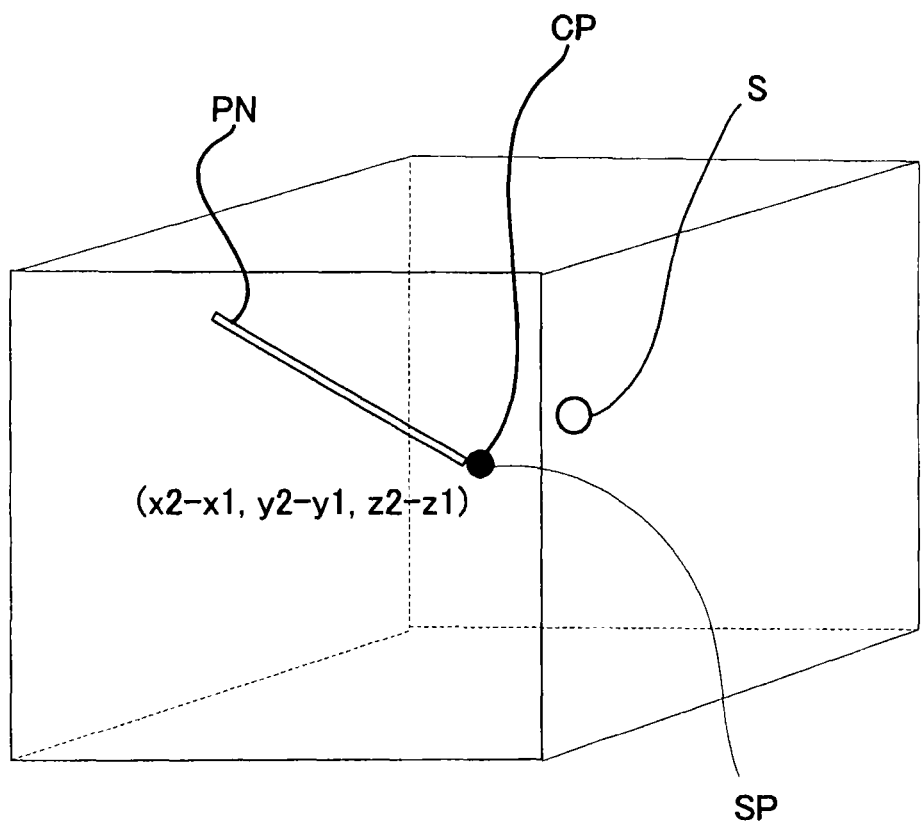
FIG. 18B is a diagram for describing the difference between coordinates of a needlepoint and coordinates of the center of scanning on the three-dimensional image.

Hereinafter, operations of the displacement calculator 720 are described with reference to FIG. 18A and FIG. 18B.

The displacement calculator 720 determines displacement between a position of the needlepoint SP of the designated puncture needle PN and a position of a center of the three-dimensional image based on the volume data. The displacement is, specifically, as shown in FIG. 18A and FIG. 18B, obtained by taking a difference (x2−x1, y2−y1, z2−z1) between coordinate values (x1, y1, z1) of the needlepoint SP and coordinate values (x2, y2, z2) of the center CP of the three-dimensional image. The above description, however, is based on the premise that, on a same coordinate, the center CP of the three-dimensional image is coincided with a scanning center SC. As described above, the displacement is derived from taking a difference between the coordinate values of the needlepoint SP and the coordinate values of the three-dimensional image center CP (Displace from FIG. 18A to FIG. 18B).

The transfer amount determinator 530 determines a relative transfer amount of the couch top 330 and the gantry apparatus 100 corresponding to the displacement obtained by the displacement calculator 520. The transfer amount is obtained by converting the earlier displacement into displacement in a real coordinate.

<Operations>

Figure 19:
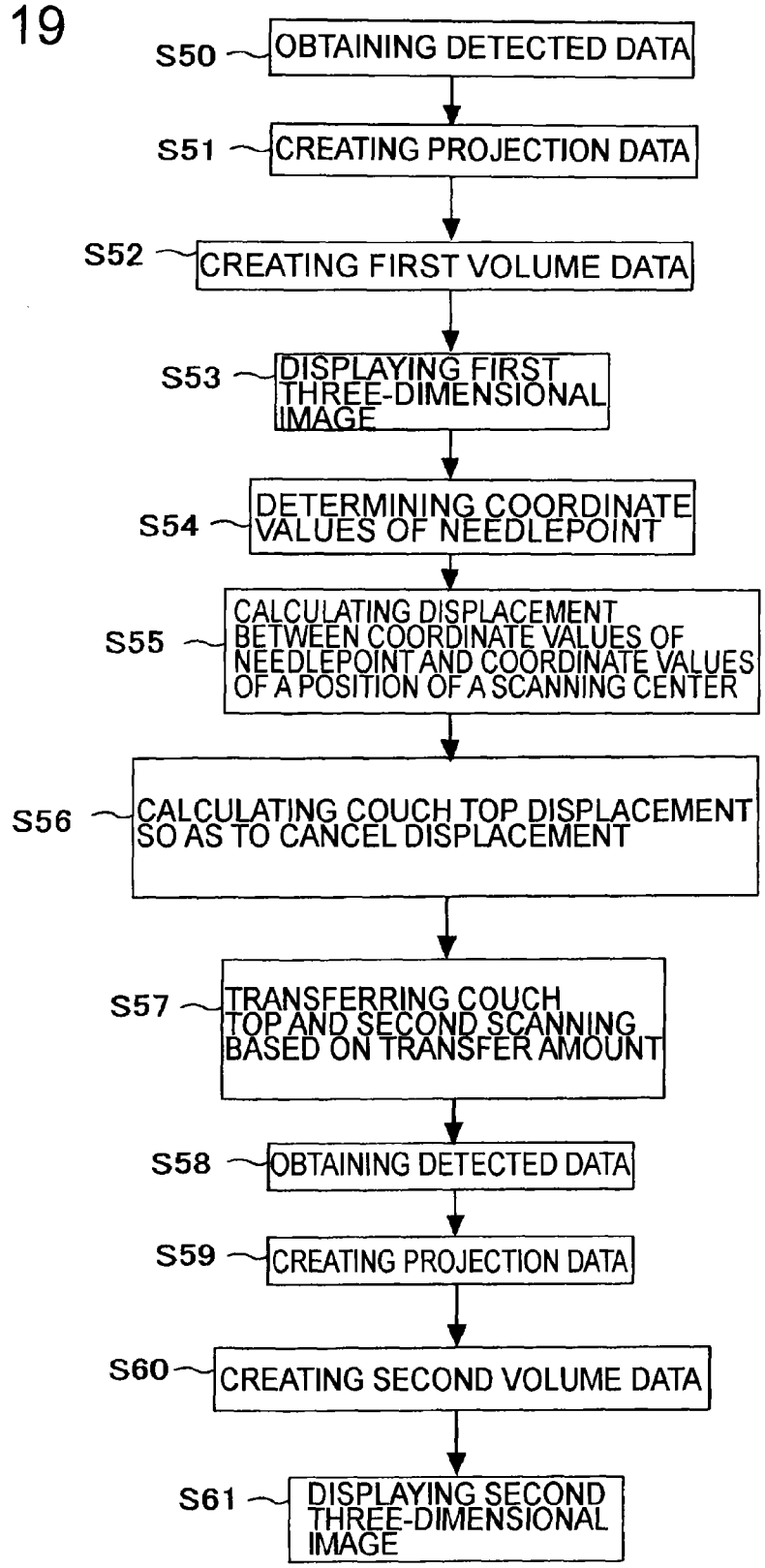
FIG. 19 is a flowchart illustrating an operation outline of the X-ray CT apparatus according to the third embodiment.

Hereinafter, as referring to FIG. 19, operations of the X-ray CT apparatus 500 according to the present embodiment are described. Here, operations are described in a case such that CT fluoroscopic imaging and puncturing are performed in alternative manner and a subject S for a puncturing work is punctured with a puncture needle PN.

In starting puncturing, first, the X-ray CT apparatus 500 performs X-ray scanning (first scanning) with respect to the subject E, and creates a first volume data.

Specifically, the X-ray generator 110 exposes X-rays with respect to the subject E. The X-ray detector 120 detects the X-rays transmitted through the subject E, and obtains detected data (S50). In the present embodiment, the detected data in one-roll is obtained. The detected data detected by the X-ray detector 120 is acquired by the data acquiring system 180, and sent to the processor 620 (preprocessor 620*a*).

The preprocessor 620*a* performs preprocessing with respect to the detected data obtained in S50, and creates projection data (S51). The created projection data is sent to the reconstruction processor 620*b* based on the control of the controller 480.

The reconstruction processor 620*b* creates a plurality of tomographic image data based on the projection data created in S51. The reconstruction processor 620*b* then creates first volume data by performing an interpolate process on the plurality of tomographic image data (S52).

The volume rendering processor 620*c* creates a first three-dimensional image by performing ray tracing with respect to the first volume data created in S52, determining brightness at each voxel (CT value), projecting image information based on the brightness onto pixels on a projection plane, and sterically-extracting internal organs, and the like to create a first three-dimensional image. The created first three-dimensional image (FIG. 18A) is displayed on the display 460 by the display controller 440. In addition, a transparentization process is performed by any of publicly known methods so as to be able to see the needlepoint of the puncture needle inside the three-dimensional image.

Next, the identifying device 710 identifies a needlepoint position SP based on the three-dimensional image, on which a puncture needle PN is drawn, created based on the volume data. The identifying device 710 then designates the identified needlepoint position SP as a needlepoint position in the display image region of the display 460. That is, the identifying device 710 determines coordinates values of the needlepoint SP of the puncture needle PN.

Further, the displacement calculator 720 determines displacement between the needlepoint position SP of the designated puncture needle PN and the center CP of the three-dimensional image based on the volume data (S55). The displacement is, specifically, as shown in FIG. 18A and FIG. 18B, obtained by taking a difference (x2−x1, y2−y1, z2−z1) between coordinate values (x1, y1, z1) of the needlepoint SP and coordinate values (x2, y2, z2) of the center CP of the three-dimensional image.

Further, the transfer amount determinator 730 determines a relative transfer amount of the couch top 330 and the gantry apparatus 100 corresponding to the displacement, so as to cancel the calculated displacement (make the scanning center position SC coincide with the needlepoint position SP of the puncture needle) (S56). The transfer amount determinator 730 then sends a second scanning starting signal (not shown) including the position information to the scan controller 410. The relative transfer amount is a difference between real coordinate values of the couch top 330 and the gantry apparatus 100 before and after transferring. The information of the transfer amount is sent to the scan controller 410 as new real coordinate values of the couch top 330 and the gantry apparatus 100 after transferring. Hereinafter, it is described the case when only the couch top 330 is transferred based on the determined transfer amount.

The scan controller 410 sends a transfer control signal Si (see FIG. 16) to the couch top 330 so as to transfer the couch top 330 by only the determined transfer amount. Upon receiving the transfer control signal Si, the couch top 330 is transferred by only the determined transfer amount by vertical transferring, back-and-forth transferring, and/or horizontal transferring. The scan controller 410 then performs X-ray scanning (second scanning) with respect to the subject E (S57).

The X-ray detector 120 detects the X-rays exposed with respect to the subject E, and obtains detected data (S58). The detected data detected by the X-ray detector 120 is acquired by the data acquiring system 180, and sent to the processor 620 (preprocessor 620a).

The preprocessor 620a performs preprocessing with respect to the detected data obtained in S58, and creates projection data (S59). The created projection data is sent to the reconstruction processor 620b based on the control of the controller 480.

The reconstruction processor 620b creates second volume data based on the projection data created in S59 (S60).

The volume rendering processor 620c creates a second three-dimensional image based on the second volume data created in S60. The created second three-dimensional image (see FIG. 18B) is displayed on the display 460 by the display controller 440 (S61).

Hereinafter, in order to verify misalignment between the needlepoint position SP of the puncture needle and the scanning center position SC when puncturing is done to some extent, the X-ray apparatus 1 again performs X-ray scanning (third scanning) with respect to the subject E, creates volume data (third volume data), and repeats the processes from S30 till S41.

<Effect>

The X-ray CT apparatus 500 of the present embodiment is an apparatus to create volume data based on a result obtained by X-ray scanning of a subject E for medical practice with a puncture needle. The X-ray CT apparatus 500 comprises the processor 620, the identifying device 710, the displacement calculator 720, the scan controller 410, and the display controller 440. The processor 620 creates a first three-dimensional image, on which the puncture needle is drawn, based on first volume data obtained by a first scanning. The identifying device 710 identifies a needlepoint position SP of the puncture needle in the first three-dimensional image. The displacement calculator 720 determines displacement between the identified needlepoint position SP and a center of the first three-dimensional image. The scan controller 410 performs second scanning by displacing the scanning center of the first scanning so as to cancel the earlier displacement. The display controller 440 allows the display 460 to display a second three-dimensional image by the processor 620 based on second volume data obtained by the second scanning.

Thus, since the needlepoint of the puncture needle can always be displayed at the center of the display screen 460a, a complete view of a region around the puncture needle can be precisely obtained. It is therefore possible to realize accuracy and efficiency in puncturing work.

Fourth Embodiment

Figure 20:
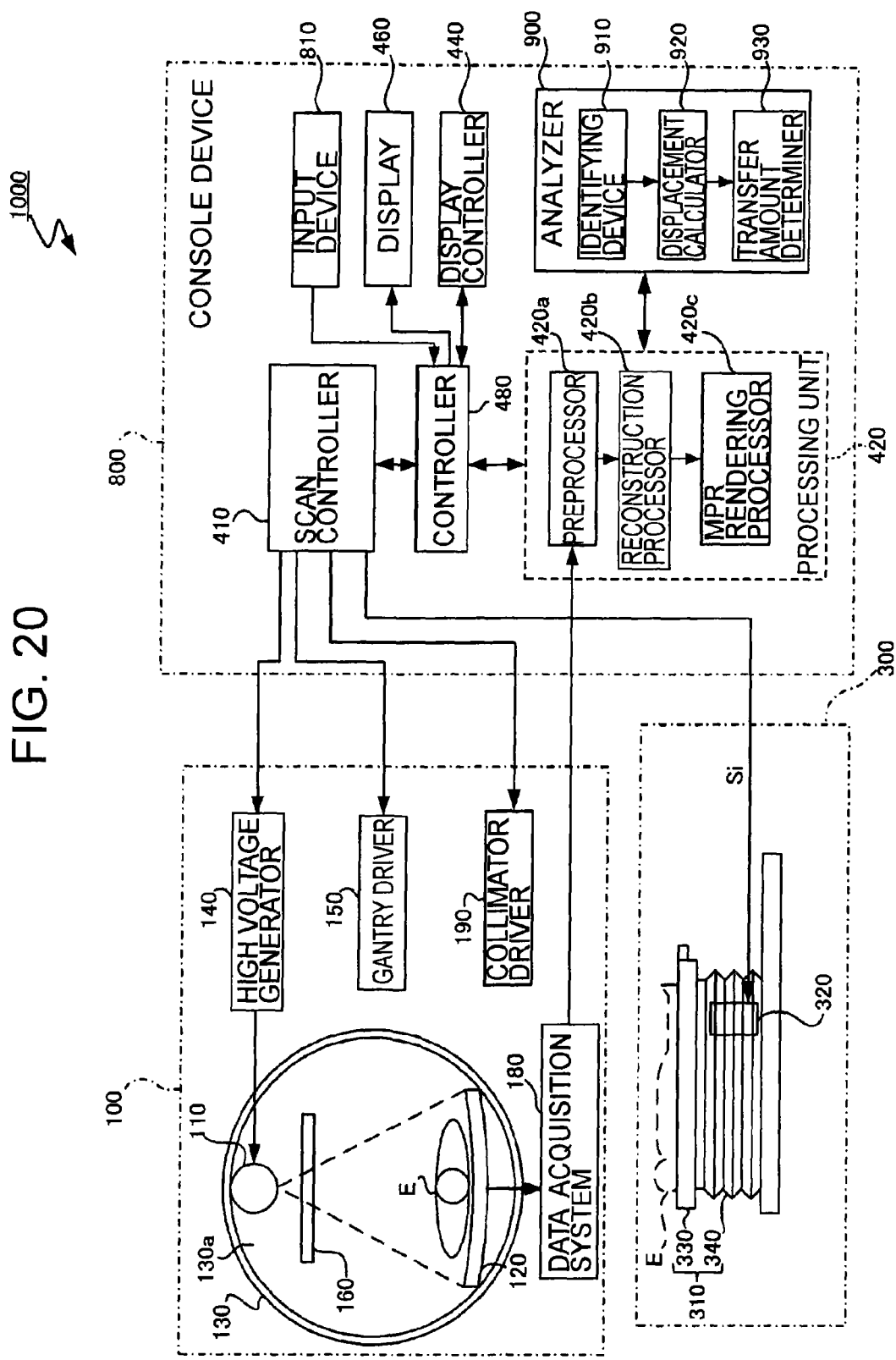
FIG. 20 is a block diagram illustrating an X-ray CT apparatus according to a forth embodiment.
Figure 21:
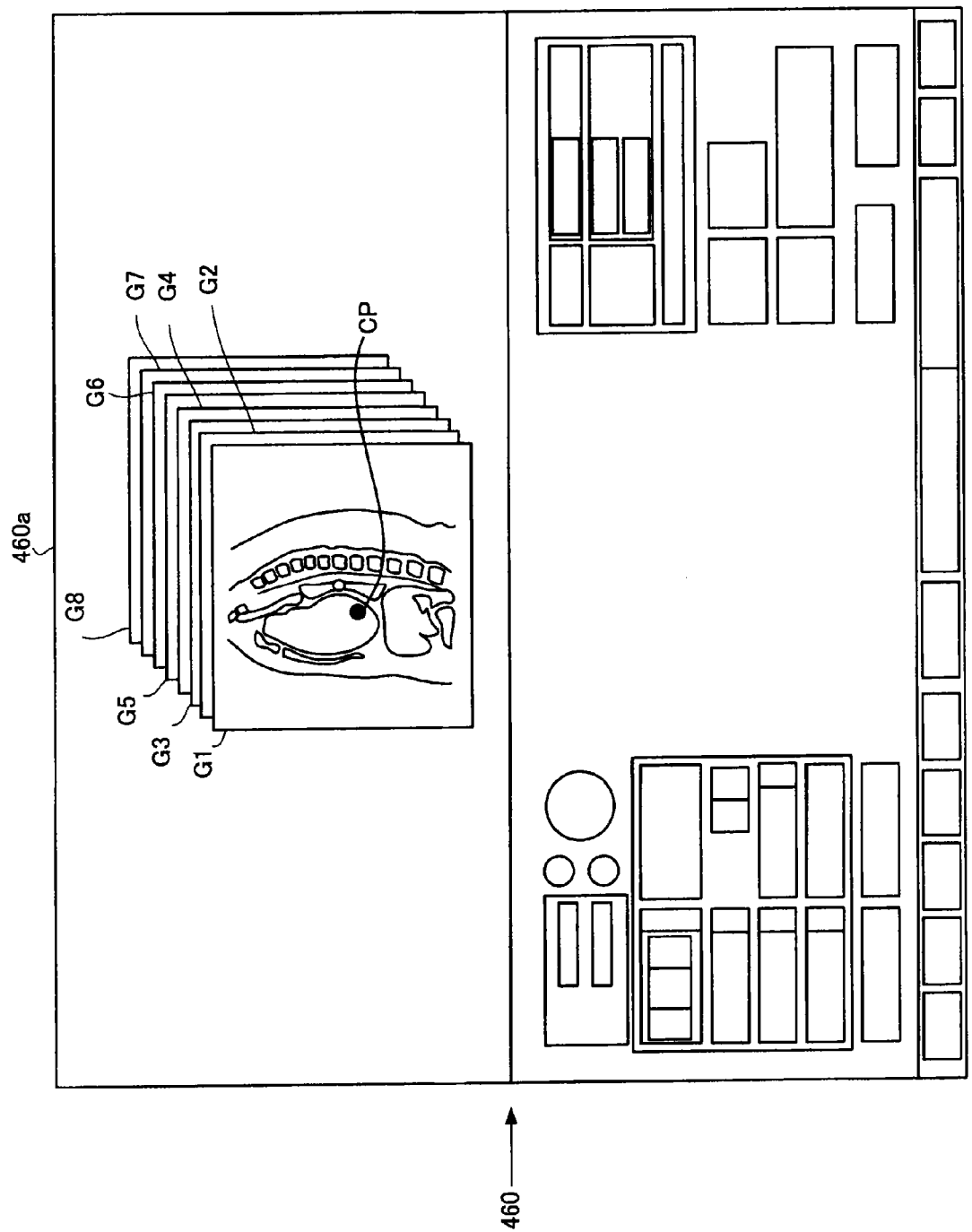
FIG. 21 is a diagram illustrating a screen of a display according to the forth embodiment.

Next, as referring to FIG. 20 and FIG. 21, configurations of an X-ray CT apparatus 1000 according to a firth embodiment are described. The X-ray CT apparatus 1000 of the present embodiment creates a plurality of MPR images based on volume data, selects a MPR image, on which a needlepoint of a puncture needle is drawn, from the created plurality of MPR images. The X-ray CT apparatus 1000 also performs a second scanning by displacing the scanning center of a first scanning so as to cancel displacement of a needlepoint position SP of the puncture needle and a scanning center position SC in the MPR image selected by an input device. Configurations of the X-ray CT apparatus 1000 is the same as those of the second embodiment above except that the input device is added and operations of a display controller and an analyzer are different. Therefore, the configurations different from those of the second embodiment are mainly described, and descriptions of the same configurations as those of the second embodiment may be omitted.

<Entire Configurations of X-Ray CT Apparatus 1000>

As shown in FIG. 20, the X-ray CT apparatus 1000 is configured to include a gantry apparatus 100, a couch apparatus 300, and a console device 800.

<Console Device>

The console device 800 is configured to include a scan controller 410, a processor 420, a display controller 440, a display 460, a controller 480, an input device 810, and an analyzer 900.

The input device 810 is used as an input device for performing a variety of operations with respect to the console device 800. The operations include, for example, selecting a MPR image, on which a puncture needle is drawn, from a plurality of MPR images displayed on the display, and identifying a position of a specific region in the MPR image. The input device 810 is configured by, for example, a keyboard, a mouse, a trackball, a joystick, or the like. As the input device 810, GUI (Graphical User Interface) displayed on the display 460 may also be used.

The MPR rendering processor 420c creates a plurality of MPR images G1 to G8 (see FIG. 21), which will be described later, by rendering first volume data created (reconstructed) by the reconstruction processor 420b in an arbitrary direction. The created plurality of MPR images G1 to G8 are displayed on the display screen 460a of the display 460 by the display controller 440.

In the present embodiment, as shown in FIG. 21, sagittal images as the MPR images G1 to G8 are displayed on the display screen 460a of the display 460. In FIG. 21, an example showing the sagittal images is shown; however, an axial image or a coronal image may be displayed. In FIG. 21, the example showing the plurality of the sagittal images is shown; however, a plurality of axial images or a plurality of coronal images may also be displayed.

The analyzer 900 is configured to include an identifying device 910, a displacement calculator 920, and a transfer amount determinator 930.

Figure 22A:
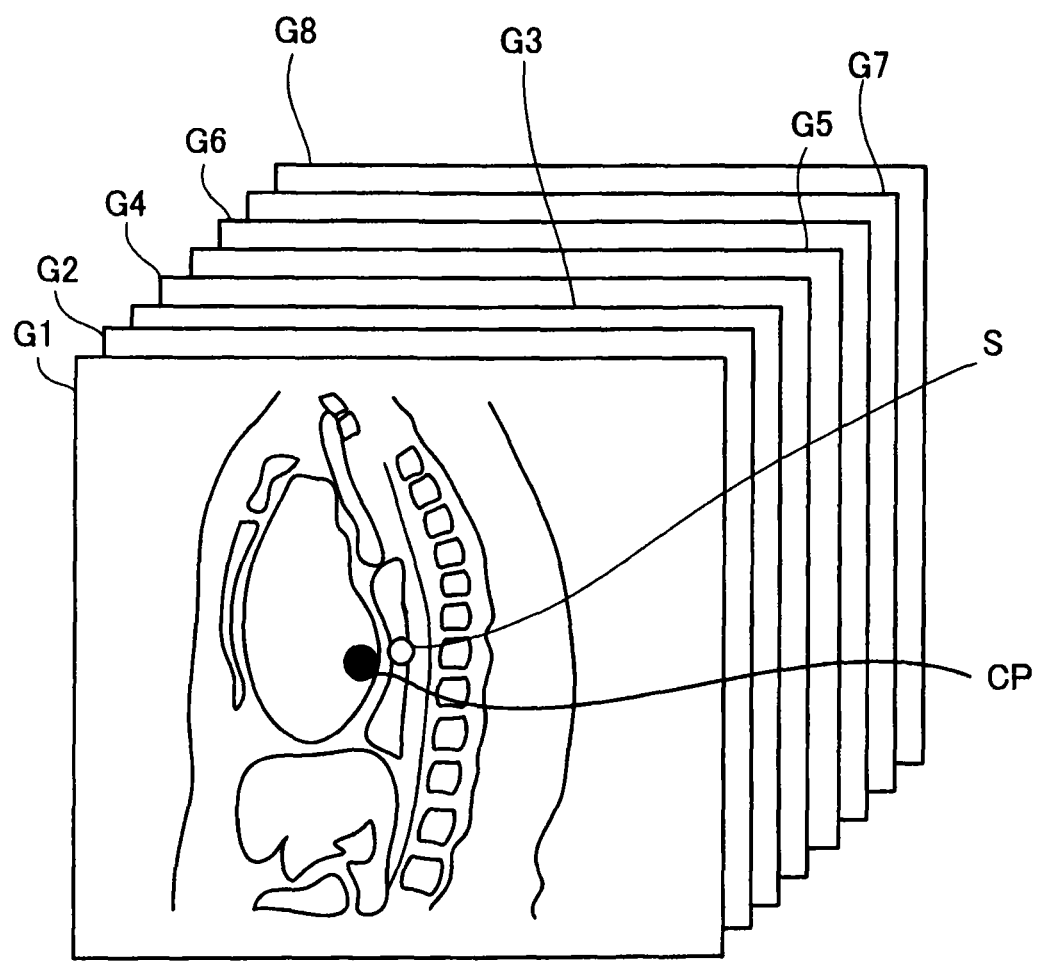
FIG. 22A is a diagram for describing changes in the screens of the display according to the forth embodiment.
Figure 22B:
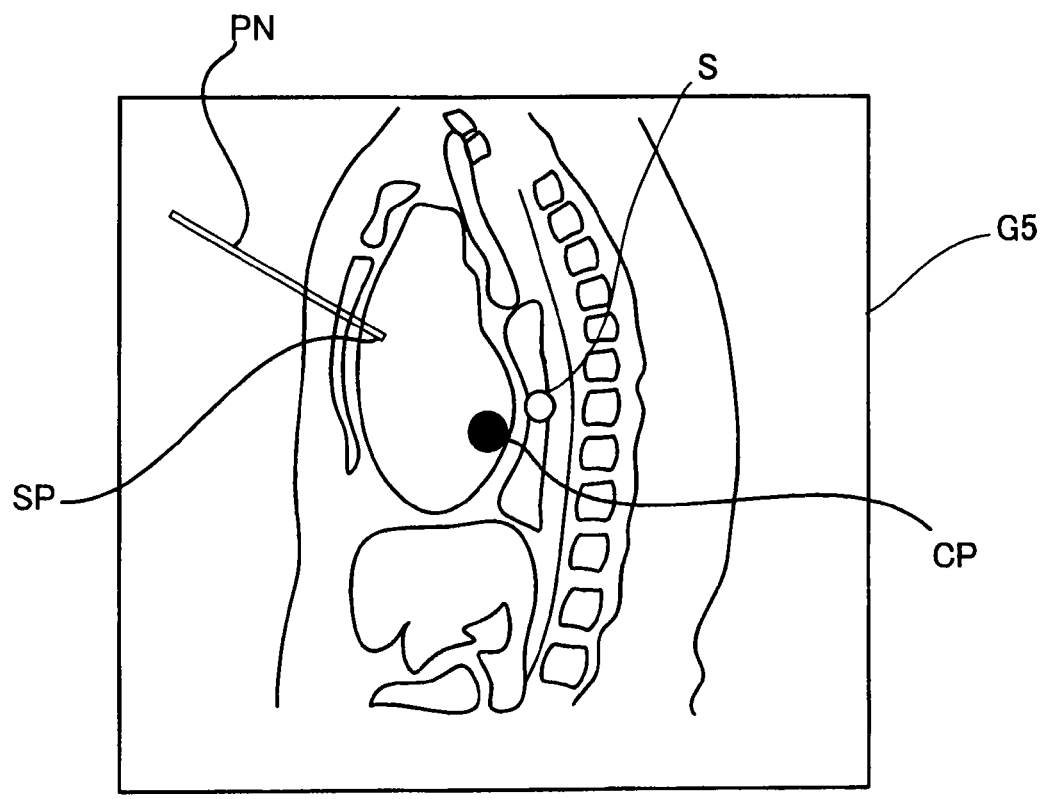
FIG. 22B is a diagram for describing changes in the screens of the display according to the forth embodiment.

The identifying device 910 identifies the MPR image, which is selected and instructed by the input device 810 from the plurality of MPR images G1 to G8 created by the MPR rendering processor 420c. In FIG. 22, among the plurality of MPR images G1 to G8, assume that the MPR image G5 is the MPR image on which a puncture needle is drawn. In that case, when the MPR image G5 is selected by the input device 810, the identifying device 910 designates the selected MPR image G5 as the MPR image on which a needlepoint is displayed.

Next, once a needlepoint position SP drawn on the MPR image G5 is selected by the input device 810, the identifying device 910 identifies the selected position as the needlepoint position SP of the puncture needle. The identifying device 910 then designates coordinate values of the identified position as the needlepoint position SP of the puncture needle in an image region. In this way, the needlepoint position SP is manually designated by selection and instruction from the input device 810.

The displacement calculator 920 determines displacement between the needlepoint SP of the designated puncture needle PN and a center CP of the MPR image. The transfer amount determinator 930 determines a relative transfer amount of the couch top 330 and the gantry apparatus 100 corresponding to the displacement obtained by the displacement calculator 920. The transfer amount is obtained by converting the earlier displacement into displacement in a real coordinate. In addition, similar to the second embodiment, the above description is based on the premise that, on a same spatial coordinate system, the MPR image center position CP is coincided with the scanning center position SC.

<Operations>

Figure 23:
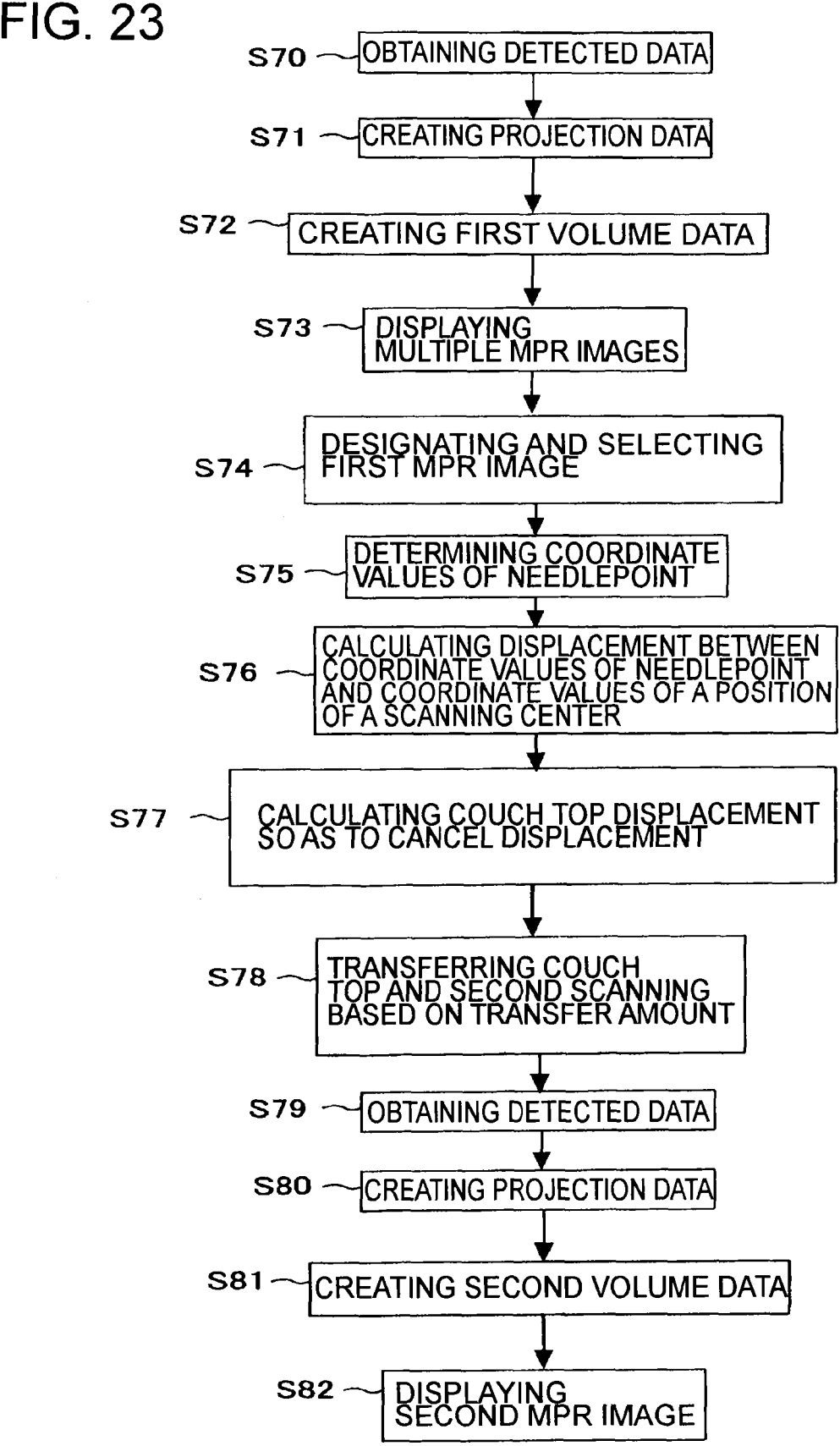
FIG. 23 is a flowchart illustrating an operation outline of the X-ray CT apparatus according to the forth embodiment.

Hereinafter, as referring to FIG. 23, operations of the X-ray CT apparatus 1000 according to the present embodiment are described. Here, operations are described in a case such that CT fluoroscopic imaging and puncturing are performed in alternative manner and a subject S for a puncturing work is punctured with a puncture needle PN.

In starting puncturing, first, the X-ray CT apparatus 1000 performs X-ray scanning (first scanning) with respect to the subject E, and creates a first volume data.

Specifically, the X-ray generator 110 exposes X-rays with respect to the subject E. The X-ray detector 120 detects the X-rays transmitted through the subject E, and obtains detected data (S70). The detected data detected by the X-ray detector 120 is acquired by the data acquiring system 180, and sent to the processor 420 (preprocessor 420a).

The preprocessor 420a performs preprocessing with respect to the detected data obtained in S70, and creates projection data (S71). The created projection data is sent to the reconstruction processor 420b based on the control of the controller 480.

The reconstruction processor 420b creates a plurality of tomographic image data based on the projection data created in S71. The reconstruction processor 420b then creates a first volume data by performing an interpolate process on the plurality of tomographic image data (S72).

The MPR rendering processor 420c creates a plurality of MPR images G1 to G8 by rendering the first volume data created (reconstructed) by the reconstruction processor 420b in an arbitrary direction. In the example in FIG. 21, the sagittal images as the MPR images G1 to G8 are displayed (S73).

In the present embodiment, an example showing the plurality of the MPR images G1 to G8 are displayed in sequence on the display screen 460a of the display 460. Specifically, the display controller 440 displays the plurality of the MPR images G1 to G8 by switching one another in rotation. The display controller 440 may also display, for example, only the MPR image G1 at first, and then display the other MPR images G2 to G8 by switching one another in rotation by selection and instruction through a switching display (selector switch, selector scroll bar) displayed at a part of the display screen 460a.

A user operates the input device 810, and selects a first MPR image G5, on which the needlepoint is drawn, from the plurality of the MPR images G1 to G8 displayed on the display 460. The identifying device 910 designates the first MPR image G5, on which the needlepoint of the puncture needle is drawn, from the first MPR image G5 selected by the input device 810 (S74. See FIG. 22B).

Next, the identifying device 910 determines coordinate values of the needlepoint of the puncture needle (S75).

The displacement calculator 920 then calculates displacement between coordinate values (X1, Y1, Z1) of the needlepoint of the puncture needle calculated and coordinate values (X2, Y2, Z2) of a scanning center position (S76).

Further, the transfer amount determinator 930 determines a relative transfer amount of the couch top 330 and the gantry apparatus 100 corresponding to the calculated displacement so as to cancel the displacement (make the scanning center position coincide with the needlepoint position SP of the puncture needle) (S77). The transfer amount determinator 730 then sends a second scanning starting signal (not shown), including the above position information to the scan controller 410. The relative transfer amount is a difference between real coordinate values of the couch top 330 and the gantry apparatus 100 before and after transferring. The information of the transfer amount is sent to the scan controller 410 as new real coordinate values of the couch top 330 and the gantry apparatus 100 after transferring.

Patterns of relative transferring of the couch top 330 and the gantry apparatus 100 include such as a case when only the couch top 330 is transferred, a case when only the gantry apparatus 100 is transferred, and a case when both the couch top 330 and the gantry apparatus 100 are transferred. Hereinafter, it is described the case when only the couch top 330 is transferred based on the determined transfer amount.

The scan controller 410 sent a transfer control signal Si (see FIG. 20) to the couch top 330 to transfer the couch top 330 by only the determined transfer amount. Upon receiving the transfer control signal Si, the couch top 330 is transferred by only the determined transfer amount by vertical transferring, back-and-forth transferring, and/or horizontal transferring. The scan controller 410 then performs X-ray scanning (second scanning) with respect to the subject E (S78).

The X-ray detector 120 detects the X-ray exposed with respect to the subject E, and obtains detected data (S79). The detected data detected by the X-ray detector 120 is acquired by the data acquiring system 180, and sent to the processor 420 (preprocessor 420*a*).

The preprocessor 420*a* performs preprocessing with respect to the detected data obtained in S78, and creates projection data (S80). The created projection data is sent to the reconstruction processor 420*b* based on the control of the controller 480.

The reconstruction processor 420*b* creates a plurality of tomographic image data based on the projection data created in S79. The reconstruction processor 420*b* also creates a second volume data by performing an interpolate process on the plurality of tomographic image data (S81).

Figure 22C:
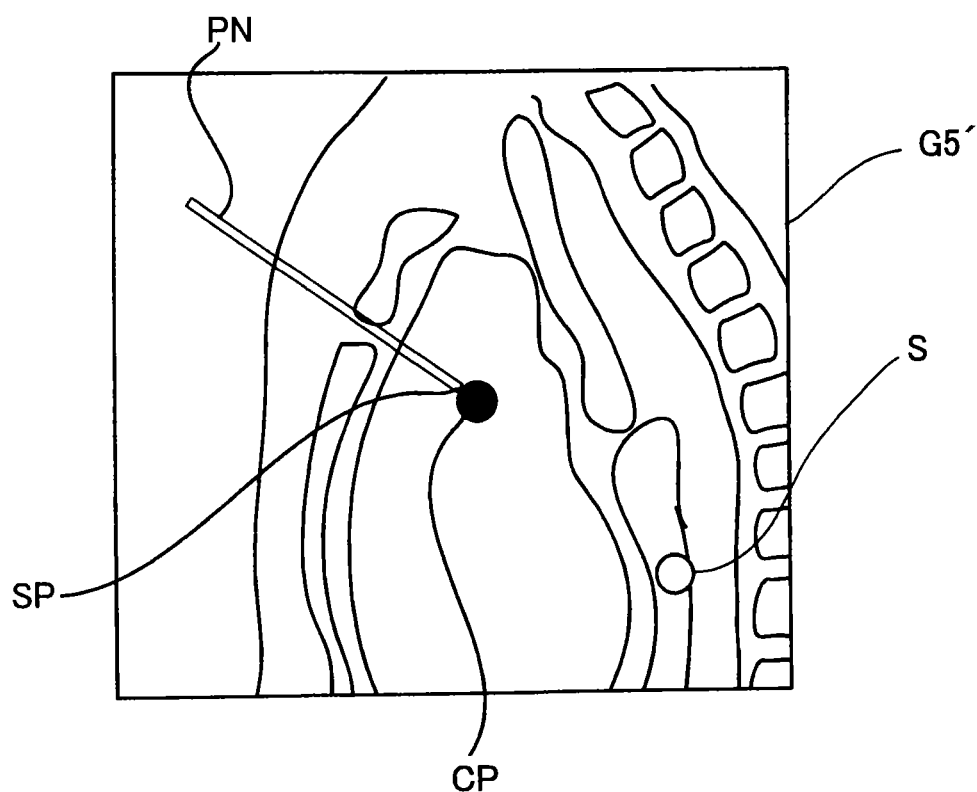
FIG. 22C is a diagram for describing changes in the screens of the display according to the forth embodiment.

The MPR rendering processor 420*c* creates a plurality of MPR images by rendering the second volume data, which is created in S81, in an arbitrary direction. Next, from those of the plurality of MPR images, the identifying device 910 designates a second MPR image G5' corresponding to the first MPR image G5. The display controller 440 allows the display 460 to display the designated second MPR image G5' on the display screen 460*a* (S82. See FIG. 22C). As shown in FIG. 22C, a needlepoint position SP of the puncture needle is coincided with a scanning center position SC in the second MPR image G5'.

Hereinafter, in order to verify misalignment between the puncture needlepoint position SP and the scanning center position when puncturing is done to some extent, the X-ray apparatus 1000 again performs X-ray scanning (third scanning) with respect to the subject E, creates volume data (third volume data), and repeats the processes from S70 till S82.

<Effect>

The X-ray CT apparatus 1000 of the present embodiment is an apparatus to create volume data based on a result obtained by X-ray scanning of a subject E for medical practice with a puncture needle PN. The X-ray CT apparatus 1000 comprises the MPR rendering processor 420*c*, the display controller 440, the identifying device 910, and the displacement calculator 920. The MPR rendering processor 420*c* creates a plurality of MPR images based on first volume data obtained by a first scanning. The display controller 440 displays the plurality of MPR images by switching one another. The input device 810 selects, according to the operations, a first MPR image, on which the puncture needle PN is drawn, from the plurality of MPR images. The identifying device 910 identifies a needlepoint position SP of the puncture needle PN in the first MPR image selected in accordance with the operation from the plurality of MPR images according to the operation. The displacement calculator 920 determines displacement between the identified needlepoint position SP and a center of the first MPR image. The scan controller 410 performs second scanning by displacing the scanning center of the first scanning so as to cancel the displacement between the needlepoint position SP and the center of the first MPR image. The display controller 440 allows the display 460 to display a second MPR image, which is created by the MPR rendering processor 420*c* based on second volume data obtained by the second scanning and is in the same cross section as the first MPR image.

Thus, since the needlepoint SP of the puncture needle PN can always be displayed at the center of the display screen 460*a*, a complete view of a region around the puncture needle PN can be precisely obtained. In addition, the MPR image on which the needlepoint is drawn can be selected from the plurality of the MPR images by switching the screen, and the needlepoint position SP can be checked and identified on the screen. It is therefore possible to realize accuracy and efficiency in the puncturing work, and improvement in degrees of freedom of screen selection.

Several embodiments of the present invention have been described; however, these embodiments are merely presented as examples, and not intended to limit the range of the invention. These novel embodiments may be implemented in other various forms, and various omissions, replacements, and changes may be made without departing from the scope of the invention. These embodiments and their modifications are included in the range and the scope of the invention and are further included in the invention set forth in Claims and the range of the equivalents thereof.

EXPLANATION OF SYMBOLS

1 X-ray CT apparatus
10 gantry apparatus
11 X-ray generator
12 X-ray detector
13 rotating body
13*a* aperture
14 high voltage generator
15 gantry driver
16 X-ray collimator device
18 data acquisition system
19 collimator driver
30 couch apparatus
32 couch driver
33 couch top
34 base
40 console device
41 scan controller
42 image processor
42*a* preprocessor
42*b* reconstruction processor
42*c* MPR rendering processor
43 setter
44 display controller
45 displacement calculator
46 display
47 image transferring device
48 controller
49 storage
E subject

The invention claimed is:

1. An X-ray CT apparatus configured to create volume data based on a result obtained by X-ray scanning of a subject for medical practice with a puncture needle, comprising:

an image processor configured to create, based on the volume data, an image of the subject obtained by scanning in a state such that the puncture needle is being inserted into the subject; and a display controller configured to cause image to be displayed on a display, wherein the image processor is configured to create a new planned image that cancels a displacement between a first position of a specific region in the image and a second position of a corresponding specific region in a first planned image, the first planned image being created based on different volume data in advance and including a set image of an insert passage for the puncture needle with respect to the subject; and the display controller is configured to cause the display to display the new planned image, instead of the first planned image, to cancel the displacement.

2. The X-ray CT apparatus according to claim 1, wherein the image processor is further configured to transfer the set image of the insert passage for the puncture needle based on the displacement; and the display controller is configured to cause the display to display a tomographic image of the subject, on which the set image of the insert passage after transferring is drawn, as the new planned image.

3. The X-ray CT apparatus according to claim 1, further comprising:
 a top plate configured to have the subject placed thereon;
 a gantry apparatus configured to perform the scanning;
 a transfer amount determiner configured to determine a relative transfer amount of the top plate and the gantry apparatus; and
 a scan controller configured to control transferring of at least one of the top plate and the gantry apparatus in accordance with the determined transfer amount.

4. An X-ray CT apparatus configured to create volume data based on a result obtained by X-ray scanning of a subject for medical practice with a puncture needle, comprising:
 a MPR processor configured Co create a first MPR image, on which the puncture needle is drawn, based on first volume data obtained by first scanning;
 an identifying device configured to identify a needlepoint position of the puncture needle in the first MPR image;
 a displacement calculator configured to determine displacement between the identified needlepoint position and a center of the first MPR image;
 a scan controller configured to perform a second scanning by displacing a scanning center of the first scanning so as to cancel the displacement; and
 a display controller configured to cause a display to display a second MPR image, which is created by the MPR processor based on second volume data obtained by the second scanning and is in a same cross section as the first MPR image.

5. The X-ray CT apparatus according to claim 4, further comprising:
 a top plate configured to have the subject placed thereon;
 a gantry apparatus configured to perform the scanning; and
 a transfer amount determiner configured to determine a relative transfer amount of the top plate and the gantry apparatus, wherein
 the scan controller is configured to control transferring of at least one of the top plate and the gantry apparatus in accordance with the determined transfer amount.

6. An X-ray CT apparatus configured to create volume data based on a result obtained by X-ray scanning of a subject for medical practice with a puncture needle, comprising:
 a processor configured to create a first three-dimensional image, on which the puncture needle is drawn, based on first volume data obtained by a first scanning;
 an identifying device configured to identify a needlepoint position of the puncture needle in the first three-dimensional image;
 a displacement calculator configured to determine displacement between the identified needlepoint position and a center of the first three-dimensional image;
 a scan controller configured to perform a second scanning by displacing a scanning center of the first scanning to cancel the displacement; and
 a display controller configured to cause a display to display a second three-dimensional image, which is created by the processor based on second volume data obtained by the second scanning.

7. The X-ray CT apparatus according to claim 6, further comprising:
 a top plate configured to have the subject placed thereon;
 a gantry apparatus configured to perform the scanning; and
 a transfer amount determiner configured to determine a relative transfer amount of the top plate and the gantry apparatus, wherein
 the scan controller is configured to control transferring of at least one of the top plate and the gantry apparatus in accordance with the determined transfer amount.

8. An X-ray CT apparatus configured to create volume data based on a result obtained by X-ray scanning of a subject for medical practice with a puncture needle, comprising:
 a MPR processor configured to create a plurality of MPR images based on first volume data obtained by a first scanning;
 a display controller configured to display the plurality of MPR images by switching one another;
 an identifying device configured to identify a needlepoint position of the puncture needle in a first MPR image selected from the plurality of MPR images in accordance with operations;
 a displacement calculator configured to determine displacement between the identified needlepoint position and a center of the first MPR image; and
 a scan controller configured to perform a second scanning by displacing a scanning center of the first scanning so as to cancel the displacement,
 wherein the display controller is configured to cause a display to display a second MPR image, which is created by the MPR processor based on second volume data obtained by the second scanning and is in a same cross section as the first image.

9. The X-ray CT apparatus according to claim 8, further comprising:
 a top plate configured to have the subject placed thereon;
 a gantry apparatus configured to perform the scanning; and
 a transfer amount determiner configured to determine a relative transfer amount of the top plate and the gantry apparatus, wherein
 the scan controller is configured to control transferring of at least one of the top plate and the gantry apparatus in accordance with the determined transfer amount.

* * * * *